(12) United States Patent
Ramsay et al.

(10) Patent No.: US 11,937,857 B2
(45) Date of Patent: Mar. 26, 2024

(54) BONE ANCHORS AND SURGICAL INSTRUMENTS WITH INTEGRATED GUIDE TIPS

(71) Applicant: DePuy Synthes Products, Inc., Raynham, MA (US)

(72) Inventors: Christopher Ramsay, West Wareham, MA (US); John DiVincenzo, South Weymouth, MA (US); Nicholas Pavento, North Attleboro, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/955,958

(22) Filed: Sep. 29, 2022

(65) Prior Publication Data

US 2023/0088995 A1     Mar. 23, 2023

Related U.S. Application Data

(63) Continuation of application No. 16/542,800, filed on Aug. 16, 2019, now Pat. No. 11,457,961, which is a
(Continued)

(51) Int. Cl.
*A61B 17/70* (2006.01)
*A61B 17/00* (2006.01)
(Continued)

(52) U.S. Cl.
CPC ...... *A61B 17/7082* (2013.01); *A61B 17/1655* (2013.01); *A61B 17/7076* (2013.01);
(Continued)

(58) Field of Classification Search
CPC ................................................ A61B 17/7082
See application file for complete search history.

(56) References Cited

U.S. PATENT DOCUMENTS 5,458,604 A    10/1995  Schmieding
5,499,986 A     3/1996  Dimarco
(Continued)

FOREIGN PATENT DOCUMENTS

EP      1570794 A1    9/2005
EP      2272451 B1    4/2012
(Continued)

OTHER PUBLICATIONS

[No Author Listed] A New Angle on Correction. Expedium. DePuy. 2009; 2 pages.
(Continued)

*Primary Examiner* — Tessa M Matthews
(74) *Attorney, Agent, or Firm* — Barnes & Thornburg LLP

(57) ABSTRACT

Bone anchors and surgical instruments (e.g., bone taps, drivers, etc.) are disclosed herein that include integrated guide tips. Use of these anchors or instruments can eliminate one or more of the steps in a conventional bone anchor installation procedure, improving surgical efficiency and safety. For example, a surgical instrument can include a guide projection configured for insertion through a cannulation formed in a bone anchor when the surgical instrument is coupled to the bone anchor. The surgical instrument can also include various mechanisms for adjusting the position of the guide projection relative to the bone anchor. The guide projection can replace the needle, stylet, and guidewire used in typical insertion procedures. The bone anchor can also include integrated tapping features to eliminate the need for a separate bone tap instrument. Thus, in some embodiments, targeting, tapping, and driving the bone anchor can be performed in a single step.

21 Claims, 18 Drawing Sheets

Related U.S. Application Data continuation of application No. 15/000,321, filed on Jan. 19, 2016, now Pat. No. 10,413,339, which is a continuation of application No. 14/156,517, filed on Jan. 16, 2014, now Pat. No. 9,289,249, which is a continuation of application No. 13/804,012, filed on Mar. 14, 2013, now Pat. No. 9,433,445.

(51) Int. Cl.
| | | |
|---|---|---|
| *A61B 17/16* | (2006.01) | |
| *A61B 17/86* | (2006.01) | |
| *A61B 17/88* | (2006.01) | |
| *A61B 90/00* | (2016.01) | |

(52) U.S. Cl.
CPC ...... *A61B 17/7092* (2013.01); *A61B 17/8635* (2013.01); *A61B 17/888* (2013.01); *A61B 17/8897* (2013.01); *A61B 2017/00469* (2013.01); *A61B 17/7037* (2013.01); *A61B 2090/034* (2016.02); *A61B 2090/061* (2016.02)

(56) References Cited

U.S. PATENT DOCUMENTS

| | | |
|---|---|---|
| 5,658,289 A | 8/1997 | Boucher et al. |
| 5,879,350 A | 3/1999 | Sherman et al. |
| 6,019,776 A | 2/2000 | Preissman et al. |
| 6,053,917 A | 4/2000 | Sherman et al. |
| 6,056,753 A | 5/2000 | Jackson |
| 6,113,601 A | 9/2000 | Tatar |
| 6,280,442 B1 | 8/2001 | Barker et al. |
| 6,402,757 B1 | 6/2002 | Moore, III et al. |
| 6,660,004 B2 | 12/2003 | Barker et al. |
| 6,736,820 B2 | 5/2004 | Biedermann et al. |
| 6,827,722 B1 | 12/2004 | Schoenefeld |
| 6,974,460 B2 | 12/2005 | Carbone et al. |
| 6,981,974 B2 | 1/2006 | Berger |
| 7,022,122 B2 | 4/2006 | Amrein et al. |
| 7,087,057 B2 | 8/2006 | Konieczynski et al. |
| 7,179,261 B2 | 2/2007 | Sicvol et al. |
| 7,186,255 B2 | 3/2007 | Baynham et al. |
| 7,207,995 B1 | 4/2007 | Vandewalle |
| 7,322,981 B2 | 1/2008 | Jackson |
| 7,325,470 B2 | 2/2008 | Kay et al. |
| 7,338,494 B2 | 3/2008 | Ryan |
| 7,445,627 B2 | 11/2008 | Hawkes et al. |
| 7,488,323 B2 | 2/2009 | Bacastow et al. |
| 7,604,643 B2 | 10/2009 | Ciccone et al. |
| 7,615,068 B2 | 11/2009 | Timm et al. |
| 7,686,833 B1 | 3/2010 | Muhanna et al. |
| 7,727,261 B2 | 6/2010 | Barker et al. |
| 7,766,946 B2 | 8/2010 | Bailly |
| 7,785,354 B2 | 8/2010 | Biedermann et al. |
| 7,789,900 B2 | 9/2010 | Levy et al. |
| 7,892,207 B2 | 2/2011 | Simonton et al. |
| 7,938,836 B2 | 5/2011 | Ainsworth et al. |
| 8,007,522 B2 | 8/2011 | Hutchinson |
| 8,092,494 B2 | 1/2012 | Butler et al. |
| 8,100,946 B2 | 1/2012 | Strausbaugh et al. |
| 8,162,989 B2 | 4/2012 | Khalili |
| 8,167,910 B2 | 5/2012 | Nilsson |
| 8,167,912 B2 | 5/2012 | Jacofsky et al. |
| 8,192,466 B2 | 6/2012 | Yue et al. |
| 8,197,517 B1 | 6/2012 | Lab et al. |
| 8,197,518 B2 | 6/2012 | Hammill, Sr. et al. |
| 8,216,243 B2 | 7/2012 | Yevmenenko et al. |
| 8,221,472 B2 | 7/2012 | Peterson et al. |
| 8,236,006 B2 | 8/2012 | Hamada |
| 8,273,112 B2 | 9/2012 | Garamszegi et al. |
| 8,282,651 B2 | 10/2012 | Ciccone et al. |
| 8,287,576 B2 | 10/2012 | Barrus |
| 8,298,274 B2 | 10/2012 | Barker, Jr. et al. |
| 8,303,601 B2 | 11/2012 | Bandeira et al. |
| 8,308,782 B2 | 11/2012 | Jackson |
| 8,313,515 B2 | 11/2012 | Brennan et al. |
| 8,313,516 B2 | 11/2012 | Konieczynski et al. |
| 8,337,530 B2 | 12/2012 | Hestad et al. |
| 8,372,076 B2 | 2/2013 | Simonton et al. |
| 8,394,108 B2 | 3/2013 | McLean et al. |
| 8,409,260 B2 | 4/2013 | Biedermann et al. |
| 8,784,431 B1 | 7/2014 | Harder et al. |
| 9,289,249 B2 | 3/2016 | Ramsay et al. |
| 9,433,445 B2 | 9/2016 | Ramsay et al. |
| 10,413,339 B2 | 9/2019 | Ramsay et al. |
| 11,457,961 B2 | 10/2022 | Ramsay et al. |
| 2002/0123752 A1 | 9/2002 | Schultheiss et al. |
| 2003/0013936 A1 | 1/2003 | Jackson, III |
| 2003/0055426 A1 | 3/2003 | Carbone et al. |
| 2005/0216027 A1 | 9/2005 | Suh et al. |
| 2006/0133889 A1 | 6/2006 | Warner |
| 2007/0016219 A1 | 1/2007 | Levine |
| 2007/0162046 A1 | 7/2007 | Vandewalle |
| 2007/0266529 A1 | 11/2007 | Paul |
| 2008/0045970 A1 | 2/2008 | Saidha et al. |
| 2008/0119852 A1 | 5/2008 | Dalton et al. |
| 2008/0147128 A1 | 6/2008 | Fritzinger |
| 2008/0154277 A1 | 6/2008 | Machalk et al. |
| 2008/0177335 A1 | 7/2008 | Melkent |
| 2008/0200635 A1 | 8/2008 | Beckwith et al. |
| 2008/0243190 A1 | 10/2008 | Dziedzic et al. |
| 2008/0269558 A1 | 10/2008 | Yahagi et al. |
| 2008/0269809 A1 | 10/2008 | Garamszegi |
| 2009/0018591 A1 | 1/2009 | Hawkes et al. |
| 2009/0187194 A1 | 7/2009 | Hamada |
| 2009/0198280 A1 | 8/2009 | Spratt et al. |
| 2009/0248029 A1 | 10/2009 | Paulos |
| 2009/0275994 A1* | 11/2009 | Phan ............... B25B 23/101 606/103 |
| 2009/0287261 A1 | 11/2009 | Jackson |
| 2010/0114111 A1 | 5/2010 | Tan-Malecki et al. |
| 2010/0114174 A1 | 5/2010 | Jones et al. |
| 2010/0121386 A1 | 5/2010 | Peultier et al. |
| 2010/0160977 A1 | 6/2010 | Gephart et al. |
| 2010/0198270 A1 | 8/2010 | Barker et al. |
| 2010/0198272 A1 | 8/2010 | Keyer et al. |
| 2010/0241124 A1 | 9/2010 | Housman et al. |
| 2010/0312279 A1* | 12/2010 | Gephart ........... A61B 17/00234 606/279 |
| 2011/0054537 A1 | 3/2011 | Miller et al. |
| 2011/0060369 A1 | 3/2011 | Assell et al. |
| 2011/0238069 A1 | 9/2011 | Zajac et al. |
| 2011/0245876 A1 | 10/2011 | Brumfield |
| 2011/0251597 A1 | 10/2011 | Bharadwaj et al. |
| 2011/0257692 A1 | 10/2011 | Sandstrom et al. |
| 2011/0282399 A1 | 11/2011 | Jackson |
| 2011/0288599 A1 | 11/2011 | Michielli et al. |
| 2011/0295321 A1 | 12/2011 | Hutchinson |
| 2011/0313460 A1 | 12/2011 | McLean et al. |
| 2011/0313471 A1 | 12/2011 | McLean et al. |
| 2012/0010661 A1 | 1/2012 | Farris et al. |
| 2012/0035670 A1 | 2/2012 | Jackson et al. |
| 2012/0089194 A1 | 4/2012 | Strausbaugh et al. |
| 2012/0191144 A1 | 7/2012 | Peultier et al. |
| 2012/0197313 A1 | 8/2012 | Cowan |
| 2012/0253404 A1 | 10/2012 | Timm et al. |
| 2012/0265156 A1 | 10/2012 | Devereux et al. |
| 2012/0283785 A1 | 11/2012 | Yevmenenko et al. |
| 2012/0303070 A1 | 11/2012 | Jackson |
| 2012/0310290 A1 | 12/2012 | Jackson |
| 2012/0316605 A1 | 12/2012 | Palagi |
| 2012/0330364 A1 | 12/2012 | Jacofsky et al. |
| 2013/0012954 A1 | 1/2013 | Paroth et al. |
| 2013/0053901 A1 | 2/2013 | Cormier et al. |
| 2013/0096618 A1 | 4/2013 | Chandanson et al. |
| 2013/0310842 A1 | 11/2013 | Winkler et al. |
| 2014/0094849 A1 | 4/2014 | Spratt et al. |
| 2014/0094862 A1 | 4/2014 | Cormier et al. |
| 2014/0276894 A1 | 9/2014 | Ramsay et al. |
| 2014/0277164 A1 | 9/2014 | Ramsay et al. |
| 2015/0045769 A1 | 2/2015 | Cabrera Aquino et al. |
| 2016/0135856 A1 | 5/2016 | Ramsay et al. |

(56) References Cited

U.S. PATENT DOCUMENTS

2018/0132920 A1   5/2018   Vikinsky et al.
2019/0365434 A1   12/2019  Ramsay et al.

FOREIGN PATENT DOCUMENTS

| EP | 2289433 B1 | 5/2017 |
|---|---|---|
| WO | 2008021771 A2 | 2/2008 |
| WO | 2008024937 A2 | 2/2008 |
| WO | 2011127065 A1 | 10/2011 |
| WO | 2012024665 A2 | 2/2012 |
| WO | 2013028851 A1 | 2/2013 |

OTHER PUBLICATIONS

[No Author Listed] DePuy Spine Pedicle Probe with Tap—Sold or offered for sale in 2008; 1 page.

[No Author Listed] Straight Talk with Expedium. Expedium; Jul. 2007; 10 pages.

[No Author Listed] Surgical Technique Guide and Ordering Information. Expedium. DePuy Spine Inc., Sep. 2011; 24 Pages.

[No Author Listed] Value Analysis Brief—Expedium Favored Angle Screw. DePuy Synthes Spine; Aug. 2012; 4 pages.

[No Author Listed] Viper 2 MIS Spine System. System Guide. DePuy Spine Inc., Sep. 2011; 60 pages.

European Office Action for Application No. 14713981.0, dated Mar. 9, 2018 (Docket No. 101896-1780), 10 pages.

International Search Report and Written Opinion for Application No. PCT/US2014/020120, dated Sep. 1, 2014; 19 pages.

U.S. Appl. No. 13/804,012, filed Mar. 14, 2013, Bone Anchors and Surgical Instruments With Integrated Guide Tips.

U.S. Appl. No. 13/826,161, filed Mar. 14, 2013, Bone Anchor Assemblies and Methods With Improved Locking.

U.S. Appl. No. 13/827,092, filed Mar. 14, 2013, Locking Compression Members for Use With Bone Anchor Assemblies and Methods.

U.S. Appl. No. 13/828,236, filed Mar. 14, 2013, Bone Anchor Assemblies With Multiple Component Bottom Loading Bone Anchors.

U.S. Appl. No. 13/828,882, filed Mar. 14, 2013, Bottom-Loading Bone Anchor Assemblies and Methods.

U.S. Appl. No. 13/829,000, filed Mar. 14, 2013, Bottom-Loading Bone Anchor Assemblies and Methods.

U.S. Appl. No. 14/156,517, filed Jan. 16, 2014, Bottom-Loading Bone Anchor Assemblies.

U.S. Appl. No. 15/000,321, filed Jan. 19, 2014, Bone Anchors and Surgical Instruments With Integrated Guide Tips.

U.S. Appl. No. 16/542,800, filed Aug. 16, 2019, Bone Anchors and Surgical Instruments With Integrated Guide Tips.

U.S. Appl. No. 61/706,860, filed Sep. 28, 2012, Bottom-Loading Bone Anchor Assemblies and Methods.

U.S. Appl. No. 61/707,062, filed Sep. 28, 2012, Bottom-Loading Bone Anchor Assemblies.

* cited by examiner

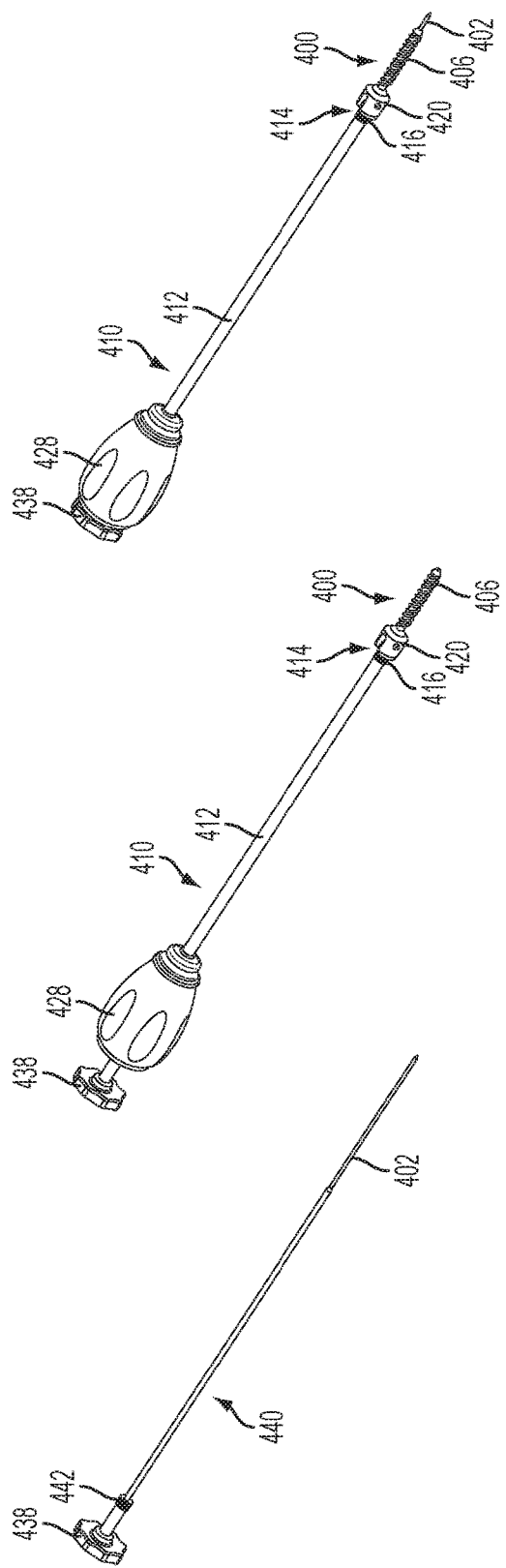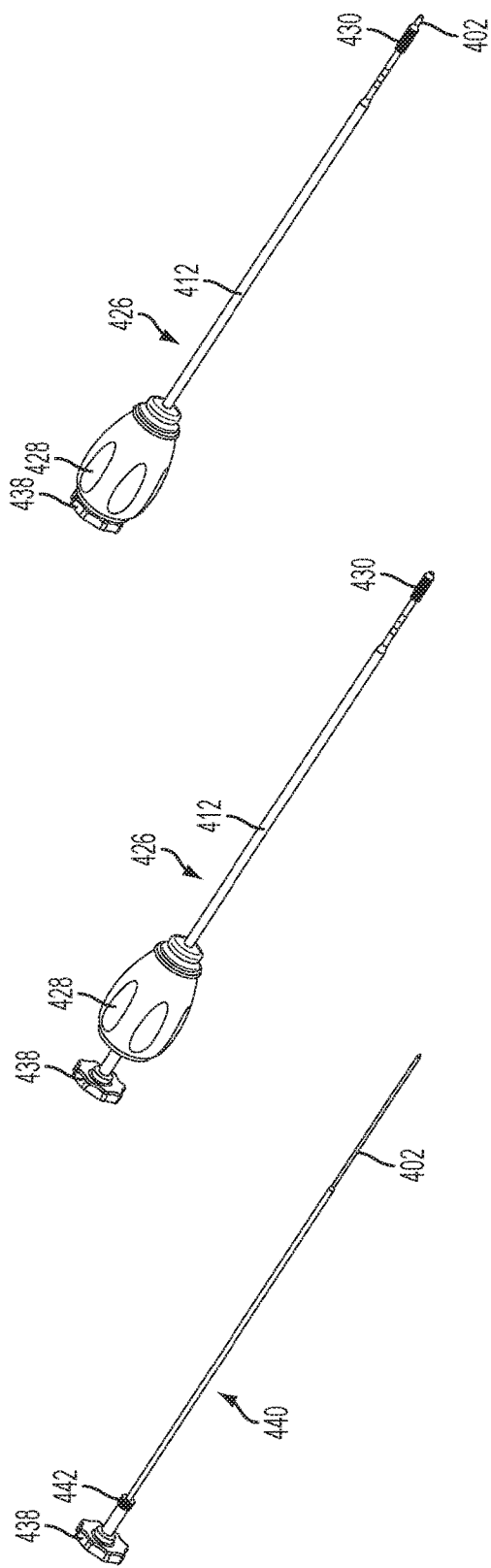
FIG. 4A  FIG. 4B  FIG. 4C  FIG. 4D  FIG. 4E  FIG. 4F

BONE ANCHORS AND SURGICAL INSTRUMENTS WITH INTEGRATED GUIDE TIPS

CROSS-REFERENCE TO RELATED APPLICATIONS

This application is a continuation of U.S. patent application Ser. No. 16/542,800, filed on Aug. 16, 2019. U.S. patent application Ser. No. 16/542,800 is a continuation of U.S. patent application Ser. No. 15/000,321 filed on Jan. 19, 2016, and now issued as U.S. Pat. No. 10,413,339. U.S. patent application Ser. No. 15/000,321 is a continuation of U.S. patent application Ser. No. 14/156,517 filed on Jan. 16, 2014 and now issued as U.S. Pat. No. 9,289,249. U.S. patent application Ser. No. 14/156,517 is a continuation of U.S. patent application Ser. No. 13/804,012 filed on Mar. 14, 2013 and now issued as U.S. Pat. No. 9,433,445. The entire contents of each of these applications is incorporated by reference herein.

FIELD

Bone anchors and associated instrumentation and methods are disclosed herein.

BACKGROUND

Bone anchors can be used in orthopedic surgery to fix bone during healing, fusion, or other processes. In spinal surgery, for example, bone anchors can be used to secure a spinal fixation element to one or more vertebrae to rigidly or dynamically stabilize the spine.

In a conventional procedure for coupling a bone anchor to bone, access to the bone is obtained, for example by forming a skin incision and resecting soft tissue disposed over the bone or by using a minimally-invasive technique. An insertion needle with a stylet disposed therein, sometimes referred to as a Jamshidi needle, is then driven into the bone to establish the trajectory for a bone opening. Next, the stylet is removed and a guidewire is inserted through the needle. The needle is then withdrawn over the guidewire, leaving the guidewire in place. A cannulated tap is then advanced over the guidewire and driven into the bone to enlarge the bone opening into a pilot hole for the bone anchor. Thereafter, the tap is withdrawn over the guidewire, again leaving the guidewire in place within the bone opening. A cannulated bone anchor is then advanced over the guidewire and driven into the bone opening. Finally, the guidewire is removed and one or more fixation elements are coupled to the bone anchor.

The conventional procedure detailed above suffers from a number of disadvantages. For example, the process involves several steps which can be time-consuming and cumbersome, particularly where a number of bone anchors are being installed. In addition, many of these steps (e.g., advancing the needle, advancing the guidewire, advancing the tap, and advancing the bone anchor) are done with fluoroscopic guidance to confirm the correct trajectory and insertion depth. With each additional step, the radiation exposure to the patient and surgical team increases, potentially causing dangerous complications or negative long-term health effects. The steps of removing the needle and removing the tap can also cause the guidewire to dislodge from the bone opening, requiring the process to be started anew. Further still, advancing the anchor or advancing the tap can inadvertently cause the guidewire to advance within the bone opening, potentially damaging delicate anatomical structures disposed in proximity to the bone. Advancing the anchor or advancing the tap can also cause the guidewire to become kinked, making removal of the guidewire very difficult. Accordingly, a need exists for improved bone anchors and associated instrumentation and methods.

SUMMARY

Bone anchors and surgical instruments (e.g., bone taps, drivers, etc.) are disclosed herein that include integrated guide tips. Use of these anchors or instruments can eliminate one or more of the steps in a conventional bone anchor installation procedure, improving surgical efficiency and safety. For example, a surgical instrument can include a guide projection configured for insertion through a cannulation formed in a bone anchor when the surgical instrument is coupled to the bone anchor. The surgical instrument can also include various mechanisms for adjusting the position of the guide projection relative to the bone anchor. The guide projection can replace the needle, stylet, and guidewire used in typical insertion procedures. The bone anchor can also include integrated tapping features to eliminate the need for a separate bone tap instrument. Thus, in some embodiments, targeting, tapping, and driving the bone anchor can be performed in a single step.

In some embodiments, a method of driving a bone anchor assembly into bone is provided. The method can include coupling an engagement portion on a driver to a corresponding engagement portion on a bone anchor assembly, the driver having a guide projection that extends distally from the engagement portion through a cannulation formed in a shank of the bone anchor assembly such that a distal tip of the guide projection protrudes from a distal end of the shank of the bone anchor assembly. The method can also include advancing the distal tip of the guide projection into bone, and driving the bone anchor assembly into the bone by rotating the driver relative to the bone.

The guide projection can be formed on a distal end of a stylus, and advancing the guide projection can include axially translating the stylus relative to the driver. The method can include rotating the stylus relative to the driver to adjust an axial position of the guide projection relative to the bone anchor assembly. Driving the bone anchor assembly can include rotating the driver relative to the bone while holding a handle portion of the stylus at a fixed rotational position relative to the bone such that the guide projection is translated axially in a proximal direction relative to the bone anchor assembly as the bone anchor assembly is advanced distally into the bone.

Advancing the guide projection can include moving a release mechanism from a first position in which the stylus can translate axially relative to the driver only when the stylus is rotated relative to the driver to a second position in which the stylus is free to translate axially relative to the driver without being rotated relative to the driver, and impacting a proximal end of the stylus to translate the stylus axially relative to the driver and advance the guide projection distally into the bone. Moving the release mechanism can include sliding a collar disposed around the driver to a position in which a lock ball retained by the collar in an opening formed in the driver is free to move radially outward from the opening to disengage the stylus.

Advancing the guide projection can include moving a release mechanism from a first position in which the stylus cannot translate axially relative to the driver to a second position in which the stylus is free to translate axially relative to the driver, and impacting a proximal end of the stylus to translate the stylus axially relative to the driver and advance the guide projection distally into the bone. Moving the release mechanism can include sliding a collar disposed around the driver to a position in which a lock ball retained by the collar in an opening formed in the driver is free to move radially outward from the opening to disengage the stylus. Sliding the collar can include rotating the collar relative to the driver or axially translating the collar relative to the driver. Advancing the guide projection can include impacting a proximal end of the stylus to cause clutch plates engaged therewith to cam over a pawl thread formed on the stylus and allow the stylus to slip distally relative to the driver.

In some embodiments, an instrument for driving a bone anchor assembly into bone is provided. The instrument can include an elongate body having proximal and distal ends, a handle portion formed at the proximal end of the elongate body, and an engagement portion formed at the distal end of the elongate body, the engagement portion being configured to engage a corresponding engagement portion on a bone anchor assembly. The instrument can include a guide projection extending distally from the engagement portion, the guide projection being configured for insertion through a cannulation formed in a shank of the bone anchor assembly.

The engagement portion can include a threaded region configured to engage a corresponding threaded portion on a rod-receiving member of a bone anchor assembly. The guide projection can be formed integrally with the elongate body. The guide projection can be formed at a distal end of a stylus positionable within a central lumen of the elongate body, the stylus being configured to mechanically engage at least one of the handle portion and the elongate body to maintain an axial position of the stylus relative to the elongate body. The stylus can be axially translatable relative to the elongate body and can be configured to translate relative to a bone anchor assembly when the engagement portion on the elongate body is coupled to an engagement portion on a bone anchor assembly.

The engagement portion on the elongate body can be coupled to an engagement portion on a bone anchor assembly, the stylus can be configured to axially translate between at least a first position in which a distal end of the guide projection protrudes from a distal end of a shank of the bone anchor assembly, and a second position in which the distal end of the guide projection does not protrude from the distal end of the shank of the bone anchor assembly. The stylus can include a threaded proximal portion configured to engage a corresponding threaded portion of the central lumen of the elongate body. The pitch of the threaded proximal portion of the stylus can be configured such that, when the engagement portion on the elongate body is coupled to an engagement portion on a bone anchor assembly, rotation of the elongate body relative to the stylus is effective to withdraw the guide projection from the bone anchor assembly at the same rate as the bone anchor assembly is advanced into the bone.

The stylus can include a proximal handle portion that is rotatable relative to the handle portion of the elongate body. The stylus can include a proximal handle portion and a length of the guide projection extending distally from the handle portion is adjustable. The handle portion of the stylus can include a release button movable between a first position in which the release button engages the guide projection to fix an axial position of the guide projection relative to the handle portion of the stylus, and a second position in which the release button does not engage the guide projection and the axial position of the guide projection relative to the handle portion of the stylus is freely-adjustable.

The instrument can include a release mechanism having a first configuration in which the stylus can translate axially relative to the elongate body only when the stylus is rotated relative to the elongate body, and a second configuration in which the stylus is free to translate axially relative to the elongate body without being rotated relative to the elongate body. The instrument can include a spring configured to bias the release mechanism towards the first configuration. The release mechanism can include a collar disposed around the elongate body and a lock ball that is retained by the collar in an opening formed in the elongate body.

The instrument can include a release mechanism having a first configuration in which the stylus cannot translate axially relative to the elongate body, and a second configuration in which the stylus is free to translate axially relative to the elongate body. The instrument can include a spring configured to bias the release mechanism towards the first configuration. The release mechanism can include a collar disposed around the elongate body and a lock ball that is retained by the collar in an opening formed in the elongate body. When the release mechanism is disposed in the first configuration, a first portion of an interior surface of the collar can be positioned adjacent to the opening formed in the elongate body, the first surface being configured to hold the lock ball in a position in which at least a portion of the lock ball extends into the central lumen of the elongate body to engage the stylus. When the release mechanism is disposed in the second configuration, a second portion of the interior surface of the collar can be positioned adjacent to the opening formed in the elongate body, the second surface being configured to allow the lock ball to move radially outward from the central lumen of the elongate body to disengage the stylus.

Translating the collar axially relative to the elongate body can be effective to move the release mechanism from the first configuration to the second configuration. Rotating the collar relative to the elongate body can be effective to move the release mechanism from the first configuration to the second configuration.

The instrument can include a clutch mechanism configured to allow the stylus to translate axially in a distal direction relative to the elongate body without requiring rotation relative to the elongate body and configured to prevent the stylus from translating axially in a proximal direction relative to the elongate body unless the stylus is rotated relative to the elongate body. The clutch mechanism can include first and second clutch plates movable into and out of engagement with the stylus, the clutch plates being biased towards a position in which they engage the stylus. The first and second clutch plates can include ratchet teeth configured to cam over a pawl thread formed on the stylus to allow the stylus to slip distally relative to the clutch plates, the ratchet teeth being further configured to catch against the pawl thread to prevent the stylus from slipping proximally relative to the clutch plates. The instrument can include a locking mechanism configured to selectively maintain the first and second clutch plates in a position in which they engage the stylus. The instrument can include a bone anchor assembly having a shank portion with a proximal threaded region and a distal threaded region, and the distal threaded region can have a major diameter that is less than a major diameter of the proximal threaded region, such that the bone anchor assembly is configured to be self-tapping.

In some embodiments, an instrument for use in cooperation with a driver shaft to advance a bone anchor assembly into bone is provided. The instrument can include a handle configured to be coupled to a proximal end of the driver shaft, and a stylus having a guide projection formed at a distal end thereof, the stylus being disposable within a lumen extending through the handle and being configured to be disposed through a lumen in a driver shaft coupled to the handle such that the guide projection is configured to extend through a cannulation formed in a bone anchor assembly when the bone anchor assembly is coupled to a distal end of the driver shaft. When the stylus is disposed through the lumen in the handle and the handle is coupled to a driver shaft having a bone anchor assembly coupled to a distal end thereof, the stylus can be axially translatable relative to the handle between at least a first position in which the guide projection is configured to protrude from a distal tip of the bone anchor assembly, and a second position in which the guide projection is configured such that it does not protrude from the distal tip of the bone anchor assembly.

In some embodiments, an instrument for use in cooperation with a bone tap to advance the bone tap into bone is provided. The instrument can include a handle configured to be coupled to a proximal end of a bone tap, and a stylus having a guide projection formed at a distal end thereof, the stylus being disposable within a lumen extending through the handle and being configured to be disposed through a lumen in a bone tap coupled to the handle. When the stylus is disposed through the lumen in the handle and the handle is coupled to a bone tap, the stylus can be axially translatable relative to the handle between at least a first position in which the guide projection is configured to protrude from a distal tip of the bone tap, and a second position in which the guide projection is configured such that it does not protrude from the distal tip of the bone tap.

In some embodiments, a bone tap is provided. The bone tap can include an elongate body having proximal and distal ends, a handle portion formed at the proximal end of the elongate body, and a threaded bone tapping region formed at the distal end of the elongate body. The bone tap can include a stylus having a guide projection formed at a distal end thereof, the stylus being positionable within a central lumen of the elongate body such that the guide projection protrudes from a distal end of the threaded bone tapping region, the stylus further being configured to mechanically engage the elongate body to maintain an axial position of the stylus relative to the elongate body.

The stylus can be configured to axially translate between at least a first position in which a distal end of the guide projection protrudes from a distal end of the bone tapping region, and a second position in which the distal end of the guide projection does not protrude from the distal end of the bone tapping region. The stylus can include a threaded proximal portion configured to engage a corresponding threaded portion of the central lumen of the elongate body. The pitch of the threaded proximal portion of the stylus can be configured such that rotation of the elongate body relative to the stylus is effective to withdraw the guide projection from the bone tapping region at the same rate as the bone tapping region is advanced into the bone. The stylus can include a proximal handle portion that is rotatable relative to the handle portion of the elongate body.

The stylus can include a proximal handle portion and wherein a length of the guide projection extending distally from the handle portion is adjustable. The handle portion of the stylus can include a release button movable between a first position in which the release button engages the guide projection to fix an axial position of the guide projection relative to the handle portion of the stylus, and a second position in which the release button does not engage the guide projection and the axial position of the guide projection relative to the handle portion of the stylus is freely-adjustable.

The bone tap can include a release mechanism having a first configuration in which the stylus can translate axially relative to the elongate body only when the stylus is rotated relative to the elongate body, and a second configuration in which the stylus is free to translate axially relative to the elongate body without being rotated relative to the elongate body. The bone tap can include a release mechanism having a first configuration in which the stylus cannot translate axially relative to the elongate body, and a second configuration in which the stylus is free to translate axially relative to the elongate body. The bone tap can include a clutch mechanism configured to allow the stylus to translate axially in a distal direction relative to the elongate body without requiring rotation relative to the elongate body and configured to prevent the stylus from translating axially in a proximal direction relative to the elongate body unless the stylus is rotated relative to the elongate body.

The present invention further provides devices and methods as claimed.

BRIEF DESCRIPTION OF THE DRAWINGS

The invention will be more fully understood from the following detailed description taken in conjunction with the accompanying drawings, in which:

FIG. 4A is a perspective view of a stylus of a driver instrument;

FIG. 4B is a perspective view of the stylus of FIG. 4A partially inserted through the instrument;

FIG. 4C is a perspective view of the stylus of FIG. 4A fully inserted through the instrument;

FIG. 4D is a perspective view of a stylus of a bone tap instrument;

FIG. 4E is a perspective view of the stylus of FIG. 4D partially inserted through the instrument;

FIG. 4F is a perspective view of the stylus of FIG. 4D fully inserted through the instrument

DETAILED DESCRIPTION

Bone anchors and surgical instruments (e.g., bone taps, drivers, etc.) are disclosed herein that include integrated guide tips. Use of these anchors or instruments can eliminate one or more of the steps in a conventional bone anchor installation procedure, improving surgical efficiency and safety. For example, a surgical instrument can include a guide projection configured for insertion through a cannulation formed in a bone anchor when the surgical instrument is coupled to the bone anchor. The surgical instrument can also include various mechanisms for adjusting the position of the guide projection relative to the bone anchor. The guide projection can replace the needle, stylet, and guidewire used in typical insertion procedures. The bone anchor can also include integrated tapping features to eliminate the need for a separate bone tap instrument. Thus, in some embodiments, targeting, tapping, and driving the bone anchor can be performed in a single step.

Certain exemplary embodiments will now be described to provide an overall understanding of the principles of the structure, function, manufacture, and use of the devices and methods disclosed herein. One or more examples of these embodiments are illustrated in the accompanying drawings. Those of skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Prior Art Bone Anchor Assembly

Figure 1A:
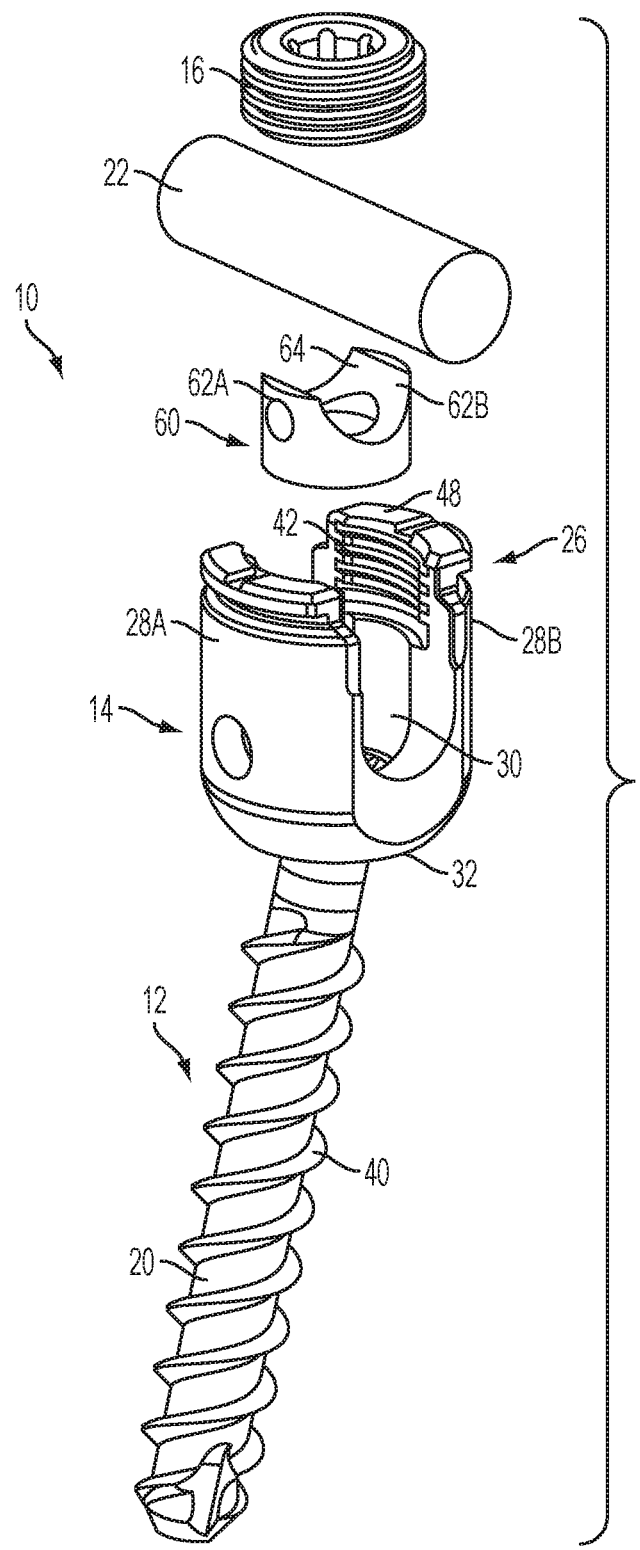
FIG. 1A is an exploded perspective view of a prior art bone anchor assembly.
Figure 1B:
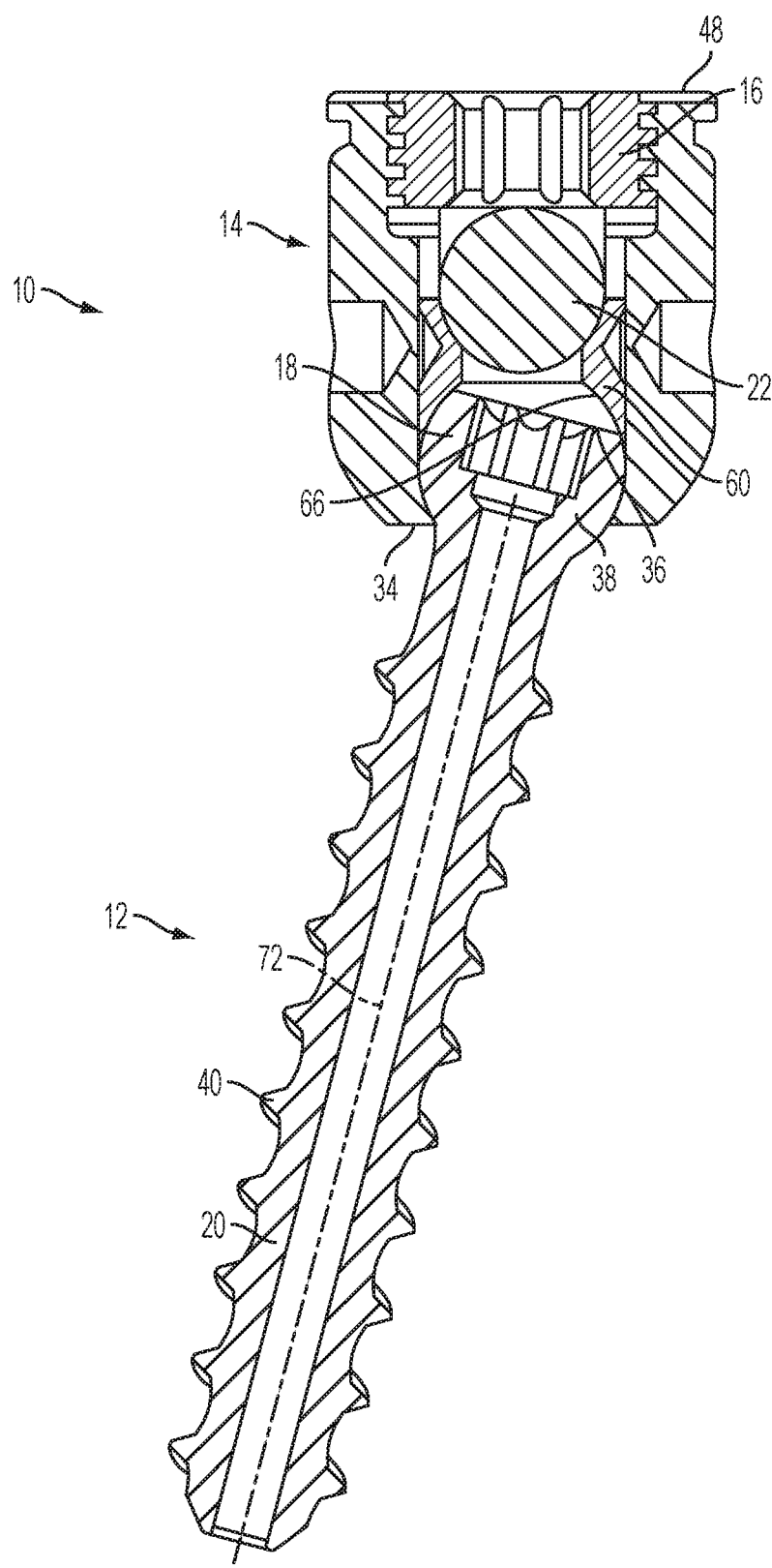
FIG. 1B is a sectional view of the prior art bone anchor assembly of FIG. 1A.

FIGS. 1A-1B illustrate a prior art bone anchor assembly 10 that includes a bone anchor 12, a receiver member 14 for receiving a spinal fixation element, such as a spinal rod 22, to be coupled to the bone anchor 12, and a closure mechanism 16 to capture a spinal fixation element within the receiver member 14 and fix the spinal fixation element with respect to the receiver member 14. The bone anchor 12 includes a proximal head 18 and a distal shaft 20 configured to engage bone. The receiver member 14 has a proximal end 26 having a pair of spaced apart arms 28A, 28B defining a recess 30 therebetween and a distal end 32 having a distal end surface 34 defining an opening through which at least a portion of the bone anchor 12 extends. The closure mechanism 16 can be positionable between and can engage the arms 28A, 28B to capture a spinal fixation element, e.g., a spinal rod 22, within the receiver member 14 and fix the spinal fixation element with respect to the receiver member 14.

The proximal head 18 of the bone anchor 12 is generally in the shape of a truncated sphere having a planar proximal surface 36 and an approximately spherically-shaped distal surface 38. The illustrated bone anchor assembly is a polyaxial bone screw designed for posterior implantation in the pedicle or lateral mass of a vertebra. The proximal head 18 of the bone anchor 12 engages the distal end 32 of the receiver member 14 in a ball and socket like arrangement in which the proximal head 18 and the distal shaft 20 can pivot relative to the receiver member 14. The distal surface 38 of the proximal head 18 of the bone anchor 12 and a mating surface within the distal end 32 of the receiver member 14 can have any shape that facilitates this arrangement, including, for example, spherical (as illustrated), toroidal, conical, frustoconical, and any combinations of these shapes.

The distal shaft 20 of the bone anchor 12 can be configured to engage bone and, in the illustrated embodiment, includes an external bone engaging thread 40. The thread form for the distal shaft 20, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Patent Application Publication No. 2013/0053901, filed on Aug. 22, 2012, both of which are hereby incorporated by reference herein. The distal shaft 20 can also include other structures for engaging bone, including a hook. The distal shaft 20 of the bone anchor 12 can be cannulated, having a central passage or cannula 72 extending the length of the bone anchor to facilitate delivery of the bone anchor over a guidewire in, for example, minimally-invasive procedures. Other components of the bone anchor assembly 10, including, for example, the closure mechanism 16, the receiver member 14, and the compression member 60 (discussed below) can be cannulated or otherwise have an opening to permit delivery over a guidewire. The distal shaft 20 can also include one or more sidewall openings or fenestrations that communicate with the cannula to permit bone in-growth or to permit the dispensing of bone cement or other materials through the bone anchor 12. The sidewall openings can extend radially from the cannula through the sidewall of the distal shaft 20. Exemplary systems for delivering bone cement to the bone anchor assembly 10 and alternative bone anchor configurations for facilitating cement delivery are described in U.S. Patent Application Publication No. 2010/0114174, filed on Oct. 29, 2009, which is hereby incorporated by reference herein. The distal shaft 20 of the bone anchor 12 can also be coated with materials to permit bone growth, such as, for example, hydroxyapatite, and the bone anchor assembly 10 can be coated partially or entirely with anti-infective materials, such as, for example, tryclosan.

The proximal end 26 of the receiver member 14 includes a pair of spaced apart arms 28A, 28B defining a U-shaped recess 30 therebetween for receiving a spinal fixation element, e.g., a spinal rod 22. Each of the arms 28A, 28B can extend from the distal end 32 of the receiver member 14 to a free end. The outer surfaces of each of the arms 28A, 28B can include a feature, such as a recess, dimple, notch, projection, or the like, to facilitate connection of the receiver member 14 to instruments. For example, the outer surface of each arm 28A, 28B can include an arcuate groove at the respective free end of the arms. Such grooves are described in more detail in U.S. Pat. No. 7,179,261, issued on Feb. 20, 2007, which is hereby incorporated by reference herein.

The distal end 32 of the receiver member 14 includes a distal end surface 34 which is generally annular in shape defining a circular opening through which at least a portion of the bone anchor 12 extends. For example, the distal shaft 20 of the bone anchor 12 can extend through the opening.

The bone anchor 12 can be selectively fixed relative to the receiver member 14. Prior to fixation, the bone anchor 12 is movable relative to the receiver member 14 within a cone of angulation generally defined by the geometry of the distal end 32 of the receiver member and the proximal head 18 of the bone anchor 12. The bone anchor 10 can be a favored angle screw, for example as disclosed in U.S. Pat. No. 6,974,460, issued on Dec. 13, 2005, and in U.S. Pat. No. 6,736,820, issued on May 18, 2004, both of which are hereby incorporated by reference herein. Alternatively, the bone anchor assembly can be a conventional (non-biased) polyaxial screw in which the bone anchor pivots in the same amount in every direction.

The spinal fixation element, e.g., the spinal rod 22, can either directly contact the proximal head 18 of the bone anchor 12 or can contact an intermediate element, e.g., a compression member 60. The compression member 60 can be positioned within the receiver member 14 and interposed between the spinal rod 22 and the proximal head 18 of the bone anchor 12 to compress the distal outer surface 38 of the proximal head 18 into direct, fixed engagement with the distal inner surface of the receiver member 14. The compression member 60 can include a pair of spaced apart arms 62A and 62B defining a U-shaped seat 64 for receiving the spinal rod 22 and a distal surface 66 for engaging the proximal head 18 of the bone anchor 12.

The proximal end 26 of the receiver member 14 can be configured to receive a closure mechanism 16 positionable between and engaging the arms 28A, 28B of the receiver member 14. The closure mechanism 16 can be configured to capture a spinal fixation element, e.g., a spinal rod 22, within the receiver member 14, to fix the spinal rod 22 relative to the receiver member 14, and to fix the bone anchor 12 relative to the receiver member 14. The closure mechanism 16 can be a single set screw having an outer thread for engaging an inner thread 42 provided on the arms 28A, 28B of the receiver member 14. In other embodiments, however, the closure mechanism 16 can include an outer set screw operable to act on the compression member 60 and an inner set screw operable to act on the rod 22.

The bone anchor assembly 10 can be used with a spinal fixation element such as rigid spinal rod 22. Alternatively, the spinal fixation element can be a dynamic stabilization member that allows controlled mobility between the instrumented vertebrae.

In use, the bone anchor assembly 10 can be assembled such that the distal shaft 20 extends through the opening in the distal end 32 of the receiver member 14 and the proximal head 18 of the bone anchor 12 is received in the distal end 32 of the receiver member 14. A driver tool can be fitted with the bone anchor 12 to drive the bone anchor 12 into bone. The compression member 60 can be positioned within the receiver member 14 such that the arms 62A, 62B of the compression member are aligned with the arms 28A, 28B of the receiver member 14 and the lower surface of the compression member 14 is in contact with the proximal head 18 of the bone anchor 12. A spinal fixation element, e.g., the spinal rod 22, can be located in the recess 30 of the receiver member 14. The closure mechanism 16 can be engaged with the inner thread 42 provided on the arms 28A, 28B of the receiver member 14. A torsional force can be applied to the closure mechanism 16 to move it within the recess 30 so as to force the spinal rod 22 into engagement with the compression member 60 and to in turn force the compression member 60 onto the proximal head 18 of the bone anchor 12, thereby fixing the spinal rod 22 relative to the receiver member 14 and locking the angular position of the bone anchor 12 relative to the receiver member 14.

The surgical instruments disclosed herein can be configured to operate in conjunction with bone anchor assemblies of the type described above or other types known in the art. In addition, one or more embodiments of inventive bone anchor assemblies are described below. Except as indicated, the structure, operation, and use of these embodiments are similar or identical to those of the bone anchor assembly 10 described above. Accordingly, a detailed description of said structure, operation, and use is omitted here for the sake of brevity.

Bone Anchors and Taps with Integrated Guide Projections

Figure 2A:
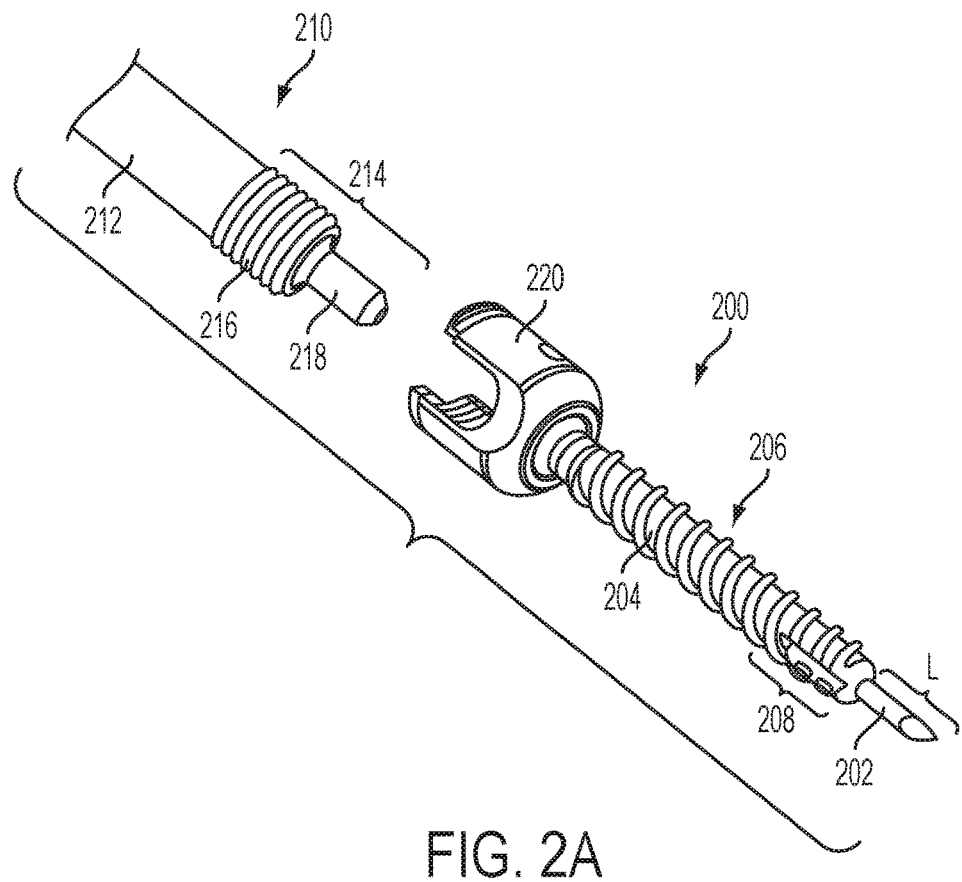
FIG. 2A is a perspective view of a driver and a bone anchor assembly with an integrated guide projection.

FIG. 2A illustrates an exemplary embodiment of a bone anchor assembly 200 that includes an integrated guide projection 202. The guide projection 202 can be formed integrally with the distal shaft 204 of the bone anchor 206, or can be selectively coupled thereto, for example using a threaded or snap fit connection. The guide projection 202 can extend a length L distally from the distal end of the shaft 204. In some embodiments, e.g., in exemplary embodiments of thoracolumbar pedicle screws, the length L can be between about 0.1 mm and about 30 mm. It will be appreciated that the length L can be selected based on a variety of factors, including the length of the bone anchor 206, the anatomy of the patient, the location at which the bone anchor assembly 200 is to be positioned, the type of procedure in which the bone anchor assembly 200 is involved, and so forth.

The guide projection 202 can be substantially cylindrical and can include a tapered or bulleted distal end that defines a sharpened point configured to penetrate bone. The distal end of the guide projection 202 can be formed by a plurality of intersecting planar faces or can be formed by a conical or frustoconical surface. The distal end of the guide projection 202 can define a beveled tip, a slash-cut tip, a diamond tip, etc. The guide projection 202 can be formed from the same material as the distal shaft 204 of the bone anchor 206, or can be formed from a separate material. Exemplary materials include titanium, titanium alloys, stainless steel, cobalt chrome, PEEK, and combinations thereof. The distal shaft 204 of the bone anchor 206 can also include one or more self-tapping features. For example, the shaft can be fluted and can include a distal portion 208 with shallower, undercut threads. In some embodiments, the undercut threads of the distal portion 208 can have a major diameter that is less than a major diameter of the proximal portion of the distal shaft 204. For example, the distal portion 208 can have a major diameter that is at least about 0.5 mm less than the major diameter of the proximal portion.

It will be appreciated that the bone anchor assembly 200 can be a monoaxial screw, a polyaxial screw, a uniplanar screw, a bone hook, a favored-angle screw, and/or any of a variety of other bone anchor types known in the art. Further information on favored-angle screws can be found in U.S. Patent Application Publication No. 2013/0096618, filed on Oct. 9, 2012, which is hereby incorporated by reference herein.

FIG. 2A also illustrates a surgical instrument 210 for driving the bone anchor assembly 200 into bone. The instrument 210 can include an elongate body 212 having an engagement portion 214 formed at a distal end thereof. The engagement portion 214 can include a threaded outer surface 216 configured to engage a corresponding threaded interior surface of the receiver member 220 of the bone anchor assembly 200. The engagement portion 214 can also include a tip 218 disposed distally of the threaded surface 216 configured to engage a drive socket or proximal surface of the bone anchor 206 or a compression cap (not shown) disposed within the receiver member 220.

Figure 2B:
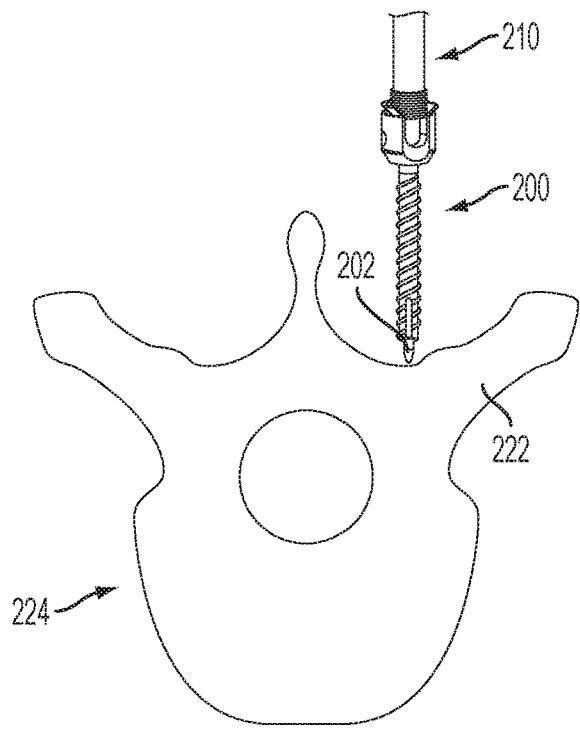
FIG. 2B is a schematic view of the bone anchor assembly of FIG. 2A positioned in proximity to a pedicle.
Figure 2C:
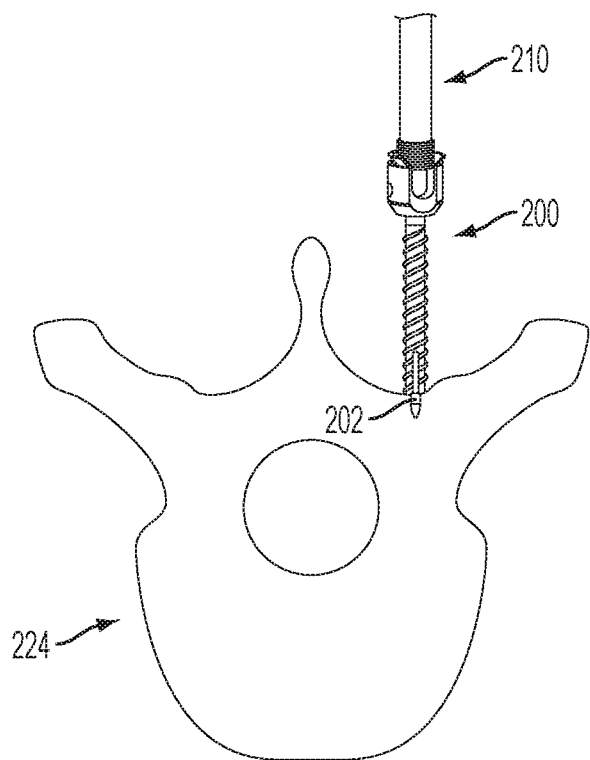
FIG. 2C is a schematic view of the bone anchor assembly of FIG. 2A positioned with the guide projection extending into the pedicle.
Figure 2D:
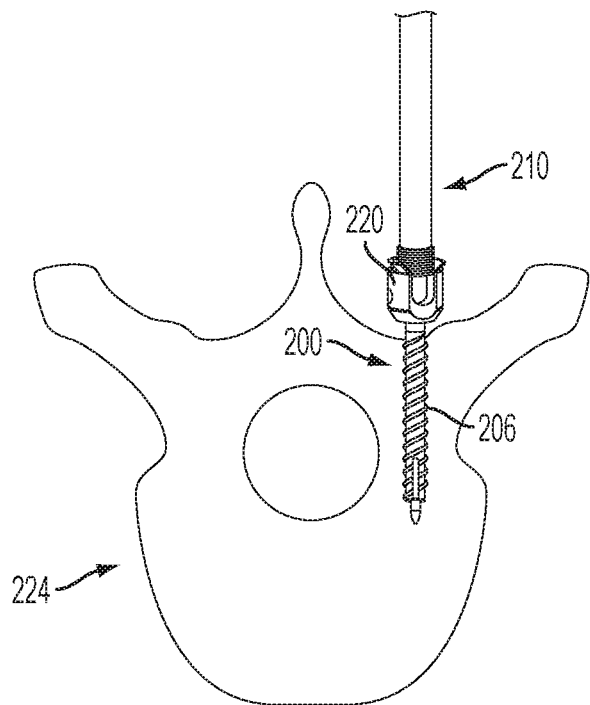
FIG. 2D is a schematic view of the bone anchor assembly of FIG. 2A after being advanced into the pedicle.

In use, an incision can be made to access the bone to which the bone anchor assembly 200 is to be coupled (e.g., a pedicle 222 of one of the patient's vertebrae 224). The bone anchor assembly 200 can be coupled to the instrument 210 and advanced through the incision to position the distal end of the guide projection 202 against the bone surface, as shown in FIG. 2B. The instrument 210 can then be tapped distally to dock the guide projection 202 in the bone 224, optionally under fluoroscopic guidance, as shown in FIG. 2C. The instrument 210 can then be rotated to advance the bone anchor 206 into the bone 224, thereby causing the distal self-tapping portion 208 of the bone anchor assembly 200 to form a pilot opening in the bone. As the bone anchor 206 is advanced further, the primary threads at the proximal portion of the bone anchor can be driven into the pilot hole, firmly securing the bone anchor to the bone 224. Before or after driving the bone anchor 206 into the bone 224, bone anchor extensions can be slid coaxially over the instrument 210 and coupled to the receiver member 220. After the bone anchor 206 is in place, as shown in FIG. 2D, the instrument 210 can be decoupled from the bone anchor assembly 200 and removed from the incision. Subsequent steps, such as affixing a spinal rod or other component to the receiver member 220 can then be performed.

Figure 2E:
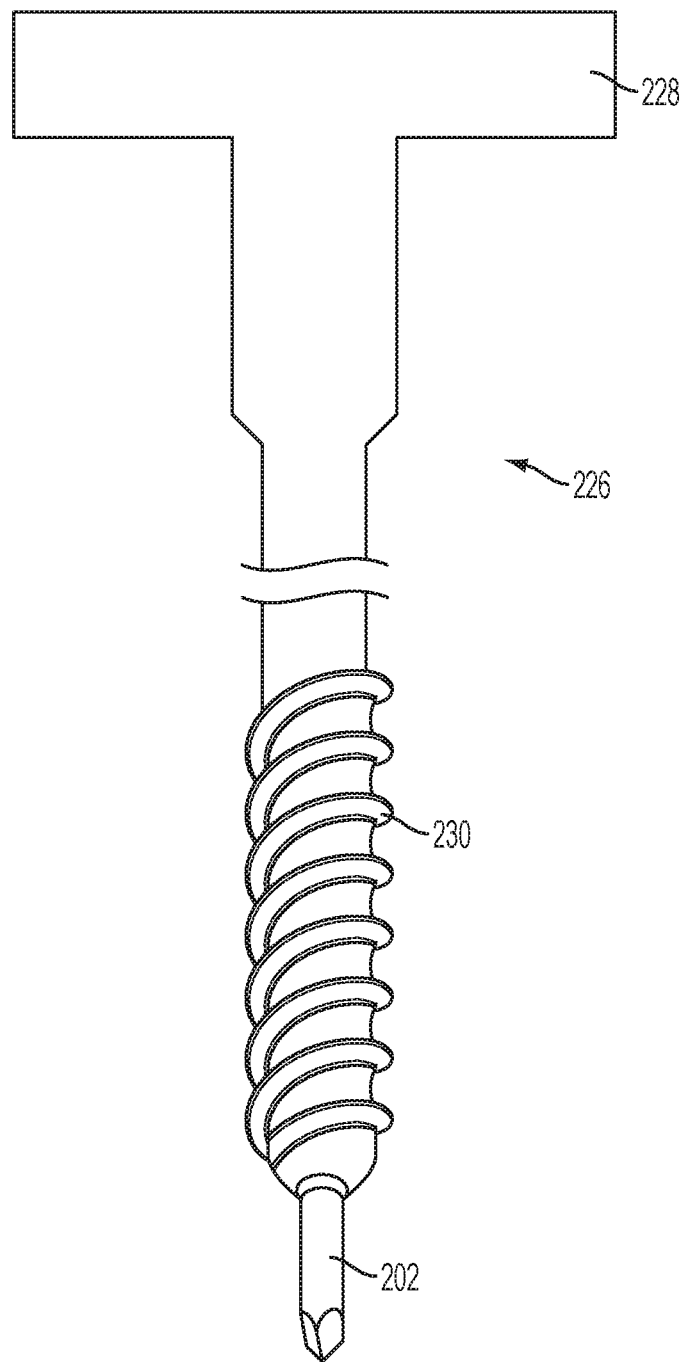
FIG. 2E is a side view of a bone tap with an integrated guide projection.

FIG. 2E illustrates an exemplary embodiment of a bone tap 226 that includes an integrated guide projection 202. As shown, the bone tap 226 can be formed with a guide projection 202 of the type described above extending distally therefrom. The proximal end of the bone tap 226 can include a handle portion 228 to allow the bone tap to be grasped by a surgeon and advanced into bone to create a pilot hole for a bone anchor. Alternatively, the bone tap 226 can include a coupling to facilitate insertion via a modular driver instrument or the surgical instrument of FIG. 2A. The distal end of the bone tap 226 can include a threaded tap surface 230 configured to form an opening in bone as it is driven into the bone.

If required by the patient anatomy or preferred by the surgeon, the method detailed above with respect to FIGS. 2A-2D can be used instead with the bone tap 226 shown in FIG. 2E to form a pilot hole before inserting the bone anchor assembly. Once the pilot hole is tapped to the desired depth using the bone tap 226, the bone tap can be removed and a conventional bone anchor assembly can be installed in the pilot hole.

Drivers with Integrated Guide Projections

Figure 3A:
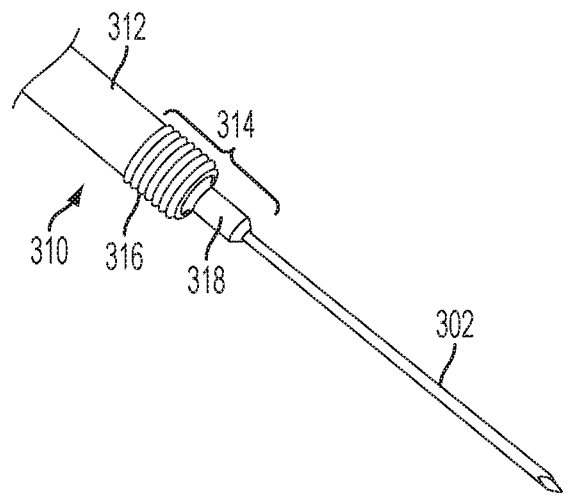
FIG. 3A is a perspective view of a driver instrument with an integrated guide projection.

FIG. 3A illustrates an exemplary embodiment of a surgical instrument 310 for driving a bone anchor assembly 300 or bone tap into bone that includes an integrated guide projection 302. The instrument 310 can include an elongate body 312 having proximal and distal ends. A handle portion (not shown) can be formed at the proximal end of the elongate body 312 to allow the instrument to be grasped by a surgeon. Alternatively, the proximal end of the elongate body 312 can include a coupling to facilitate attachment to a modular handle assembly.

An engagement portion 314 can be formed at the distal end of the elongate body 312 and can be configured to engage a bone anchor assembly 300 (e.g., a bone anchor assembly of the type described above with respect to FIGS. 1A-1B). The engagement portion 314 can include a threaded surface 316 configured to engage corresponding threads 332 formed in the receiver member 320 of the bone anchor assembly 300. The engagement portion 314 can also include a tip 318 disposed distally of the threaded surface 316 configured to engage a drive socket or a proximal surface of the bone anchor 306, or a compression cap 334 disposed within the receiver member 320. The tip 318 can have a diameter that is less than the diameter of the threaded portion 316.

Figure 3B:
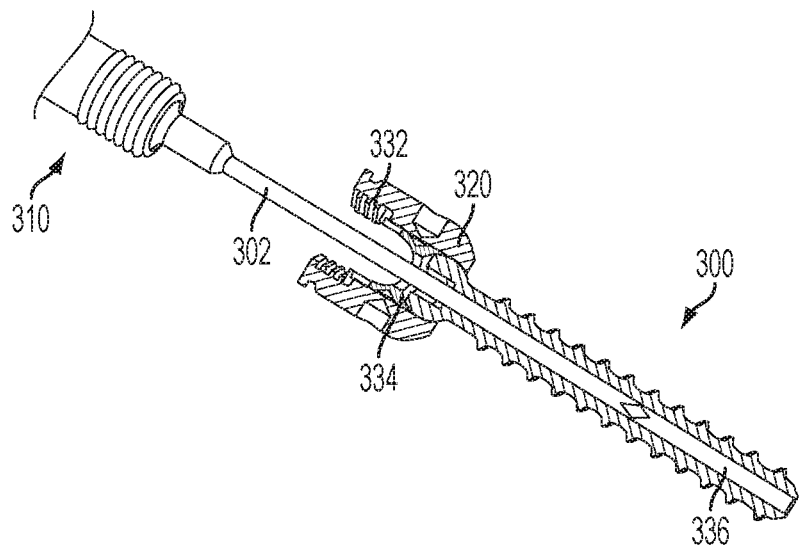
FIG. 3B is a perspective view of the instrument of FIG. 3A shown with the guide projection partially inserted through a bone anchor assembly.
Figure 3C:
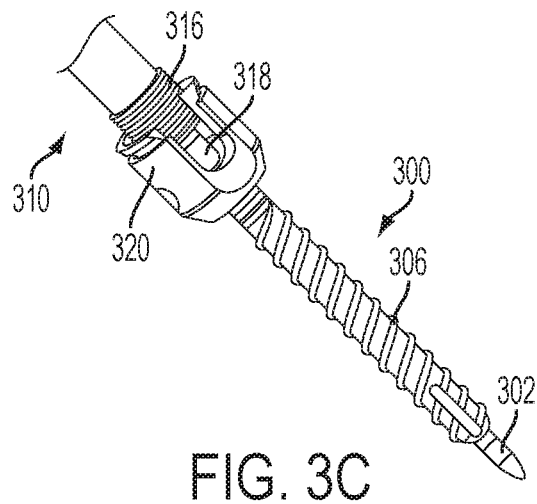
FIG. 3C is a perspective view of the instrument of FIG. 3A shown with the guide projection fully inserted through a bone anchor assembly.

The instrument 310 can also include a guide projection 302 extending distally from the engagement portion 314. The guide projection 302 can be formed integrally with the engagement portion 314 or can be selectively coupled thereto, for example using a snap-fit or threaded coupling. The guide projection 302 can be configured for insertion through a cannulation 336 formed in the bone anchor assembly 300 or in a bone tap, as shown in FIG. 3B. The guide projection 302 can have a diameter that is less than the diameter of the threaded portion 316 and/or less than the diameter of the tip 318. Thus, as shown in FIG. 3C, when the engagement portion 314 of the instrument 310 is coupled to the bone anchor assembly 300 or a bone tap, the guide projection 302 can protrude from a distal end of the bone anchor assembly 300 or the bone tap. The guide projection 302 can then be used for targeting insertion of the bone anchor assembly 300 or the bone tap.

Figure 3D:
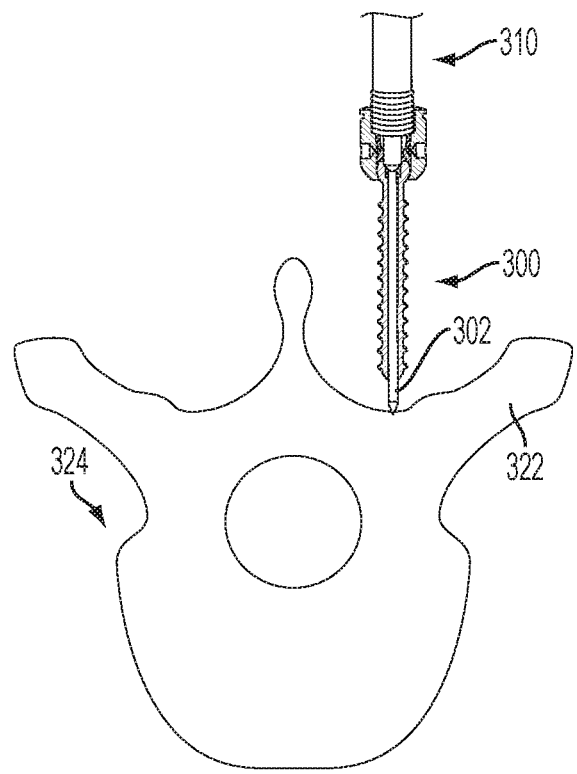
FIG. 3D is a schematic view of the instrument and bone anchor assembly of FIG. 3A positioned in proximity to a pedicle.
Figure 3E:
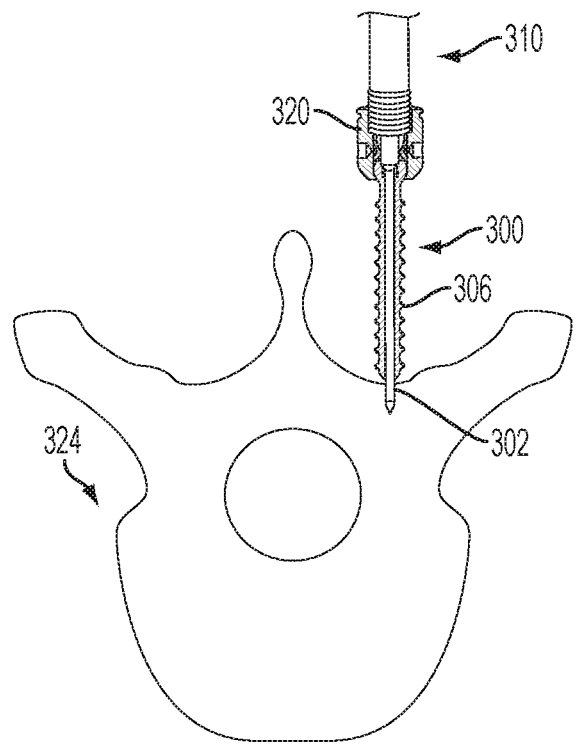
FIG. 3E is a schematic view of the instrument and bone anchor assembly of FIG. 3A positioned with the guide projection extending into the pedicle.
Figure 3F:
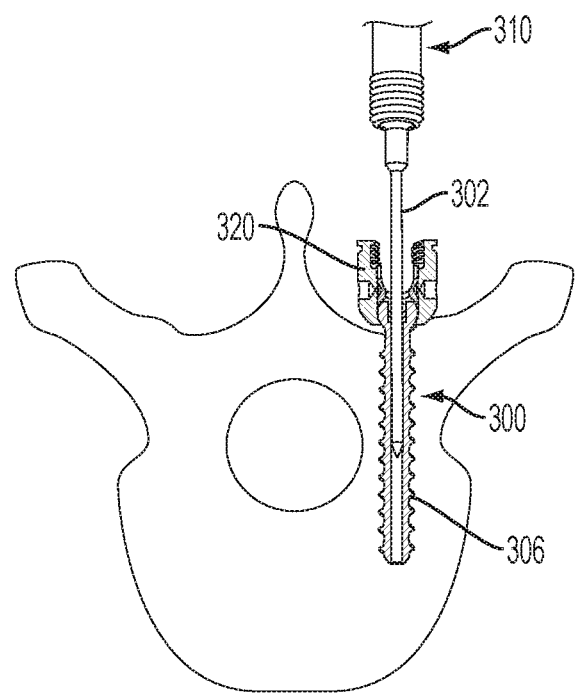
FIG. 3F is a schematic view of the instrument and bone anchor assembly of FIG. 3A after the bone anchor assembly is advanced into the pedicle.

In use, an incision can be made to access the bone to which the bone anchor assembly 300 is to be coupled (e.g., a pedicle 322 of one of the patient's vertebrae 324). A bone anchor assembly 300 or a bone tap can be coupled to the instrument 310 and advanced through the incision to position the distal end of the guide projection 302 against the bone surface, as shown in FIG. 3D. The instrument 310 can then be tapped distally to dock the guide projection 302 in the bone 324, optionally under fluoroscopic guidance, as shown in FIG. 3E. The instrument 310 can then be rotated to advance the bone anchor 306 or the bone tap into the bone. If a tap is used, the tap can be removed once a pilot hole is formed to the desired depth and can be replaced on the instrument 310 with the bone anchor assembly 300, which can then be driven into the bone 324. Before or after driving the bone anchor 306 into the bone 324, bone anchor extensions can be slid coaxially over the instrument 310 and coupled to the receiver member 320. After the bone anchor 306 is in place, as shown in FIG. 3F, the instrument 310 can be decoupled from the bone anchor assembly 300 and removed from the incision. Subsequent steps, such as affixing a spinal rod or other component to the receiver member 320 can then be performed.

Stylus with Integrated Guide Projection

FIGS. 4A-4C illustrate an exemplary embodiment of a surgical instrument 410 for driving a bone anchor 406 into bone that includes a stylus 440 having a guide projection 402 formed thereon. The instrument 410 can include an elongate body 412 having proximal and distal ends. A handle portion 428 can be formed at the proximal end of the elongate body 412 to allow the instrument to be grasped by a surgeon. Alternatively, the proximal end of the elongate body 412 can include a coupling to facilitate attachment to a modular handle assembly.

An engagement portion 414 can be formed at the distal end of the elongate body 412 and can be configured to engage a bone anchor assembly 400 (e.g., bone anchor assemblies of the type described above with respect to FIGS. 1A-1B). The engagement portion 414 can include a threaded surface 416 configured to engage corresponding threads formed in the receiver member 420 of the bone anchor assembly 400. The engagement portion 414 can also include a tip (not shown) disposed distally of the threaded surface 416 configured to engage a drive socket or a proximal surface of the bone anchor 406 or a compression cap disposed within the receiver member 420. The tip can have a diameter that is less than the diameter of the threaded portion 416.

The elongate body 412 can be hollow or can include a central axial lumen extending longitudinally therethrough in which the stylus 440 can be positioned. The stylus 440 can include a proximal handle portion 438 and a threaded portion 442 disposed adjacent to the proximal handle portion. The threaded portion 442 of the stylus 440 can be configured to engage a corresponding threaded portion of the central lumen of the elongate body 412. The threaded coupling between the stylus 440 and the elongate body 412 can secure the stylus to the elongate body and allow the stylus to be translated axially relative to the elongate body by rotating the handle portion 438 of the stylus relative to the handle portion 428 of the elongate body.

The stylus 440 can include a guide projection 402 formed at the distal end thereof. The guide projection 402 can be formed integrally with the stylus 440 or can be selectively coupled thereto, for example using a snap-fit or threaded coupling. The guide projection 402 can be configured for insertion through a cannulation formed in the bone anchor assembly 400. The guide projection 402 can have a diameter that is less than the diameter of the threaded portion 416 and/or less than the diameter of the tip of the engagement portion 414. The stylus 440 can be axially translatable between at least a first position in which the distal end of the guide projection 402 protrudes from the distal end of the bone anchor assembly 400 and a second position in which the distal end of the guide projection does not protrude from the distal end of the bone anchor assembly. The axial position of the guide projection 402 relative to the distal tip of the bone anchor assembly 400 can be adjusted by translating the stylus 440 proximally or distally relative to the elongate body 412. In some embodiments, this axial translation can be accomplished by rotating the stylus 440 relative to the elongate body 412 in a first direction to advance the stylus along a threaded surface of the elongate body and by rotating the stylus in a second, opposite direction to retract the stylus along the threaded surface. While a threaded coupling between the stylus 440 and the elongate body 412 is illustrated, it will be appreciated that other couplings can be used instead or in addition. Such couplings can allow for selective axial translation, or can be configured to hold the stylus 440 in a fixed axial position relative to the elongate body 412 (e.g., in a position in which the distal tip of the guide projection 402 protrudes from the distal end of the bone anchor 406 when the bone anchor is coupled to the elongate body). The degree to which the distal tip of the guide projection 402 protrudes from the distal end of the bone anchor 406 can vary. In some embodiments, e.g., in exemplary embodiments of thoracolumbar pedicle screws, the guide projection can extend beyond the distal tip of the bone anchor 406 up to a maximum dimension between about 0.1 mm and about 100 mm. It will be appreciated that the amount of protrusion can be adjustable, as detailed above, and that the maximum amount of protrusion can be selected based on a variety of factors, including the length of the bone anchor 406, the anatomy of the patient, the location at which the bone anchor assembly 400 is to be positioned, the type of procedure in which the bone anchor assembly 400 is involved, and so forth.

FIGS. 4D-4F illustrate an exemplary embodiment of a surgical instrument 426 for driving a bone tap 430 into bone. The instrument 426 of FIGS. 4D-4F is identical to that of FIGS. 4A-4C, except that it is configured to drive a bone tap 430 instead of a bone anchor assembly 400. The bone tap 430 can be formed integrally with the elongate body 412, or can be coupled to an engagement portion thereof, e.g., via a threaded or snap-fit connection.

Figure 4G:
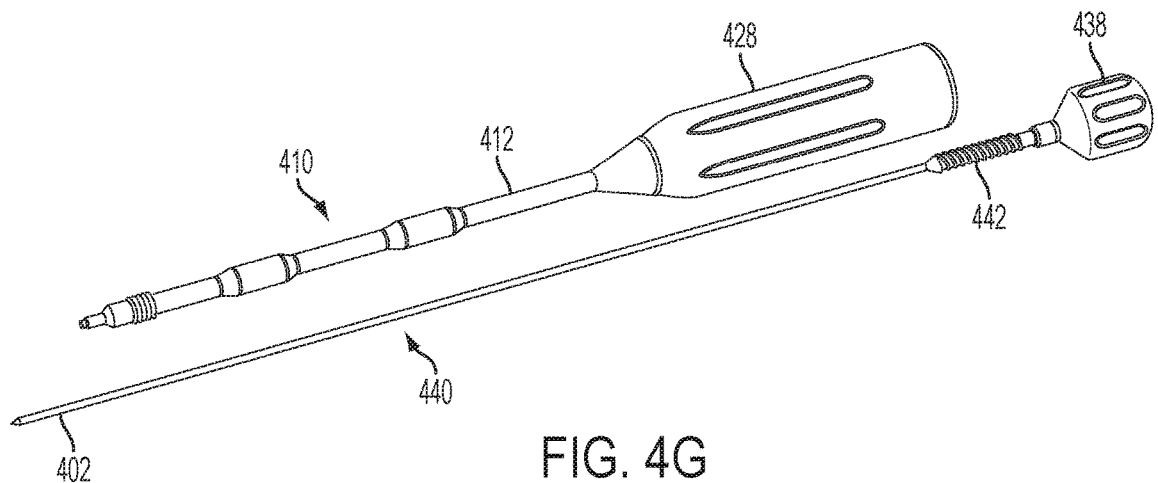
FIG. 4G is an exploded view of a driver instrument that includes a stylus.
Figure 4H:
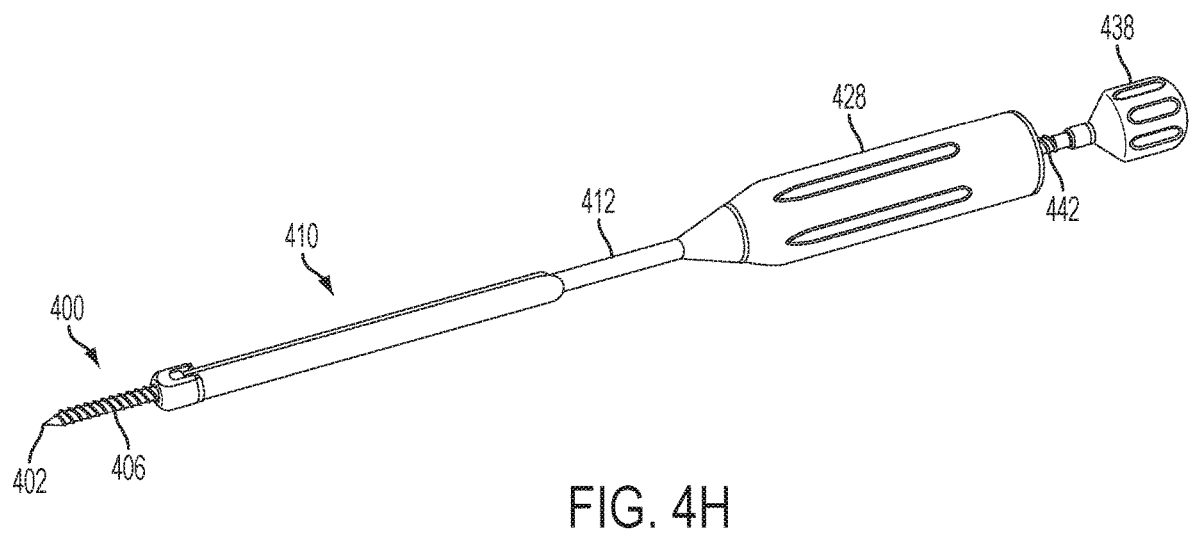
FIG. 4H is a perspective view of the instrument of FIG. 4C coupled to a bone anchor assembly.
Figure 5A:
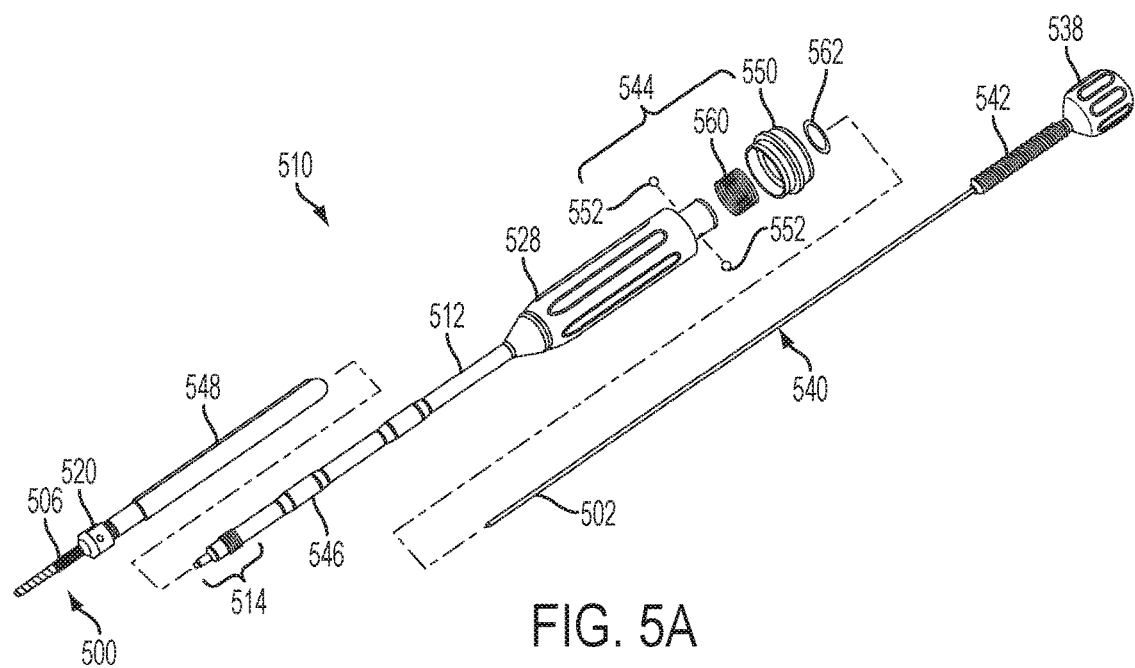
FIG. 5A is an exploded view of a bone anchor assembly and an instrument for driving the bone anchor assembly that includes a release mechanism.
Figure 5B:
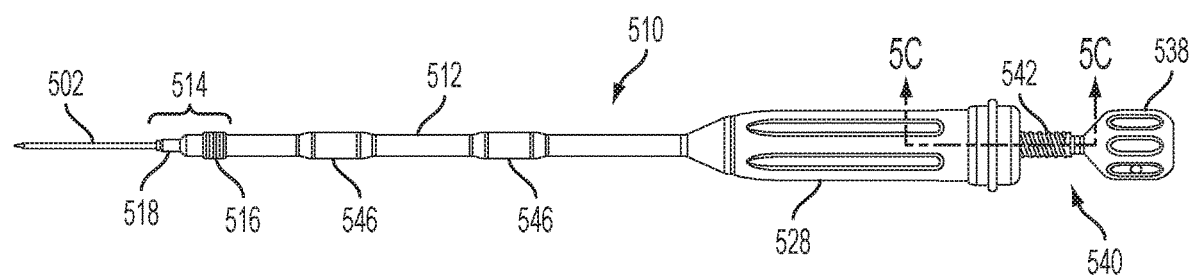
FIG. 5B is a side view of the instrument of FIG. 5A.
Figure 5C:
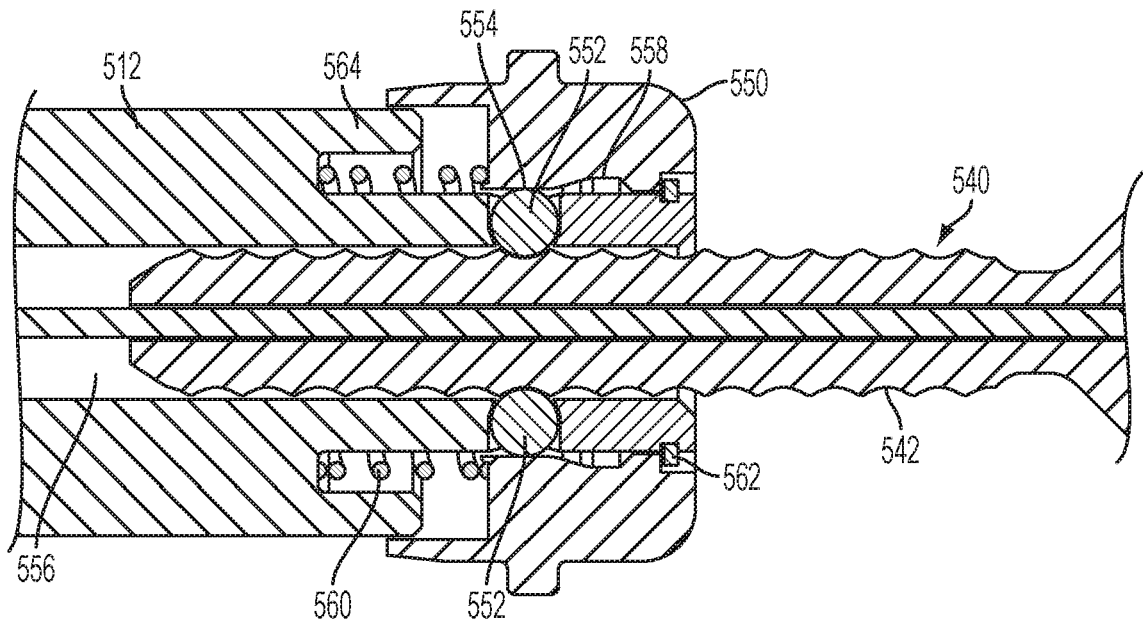
FIG. 5C is a longitudinal sectional view of the instrument of FIG. 5A shown with the release mechanism in a first position.
Figure 5D:
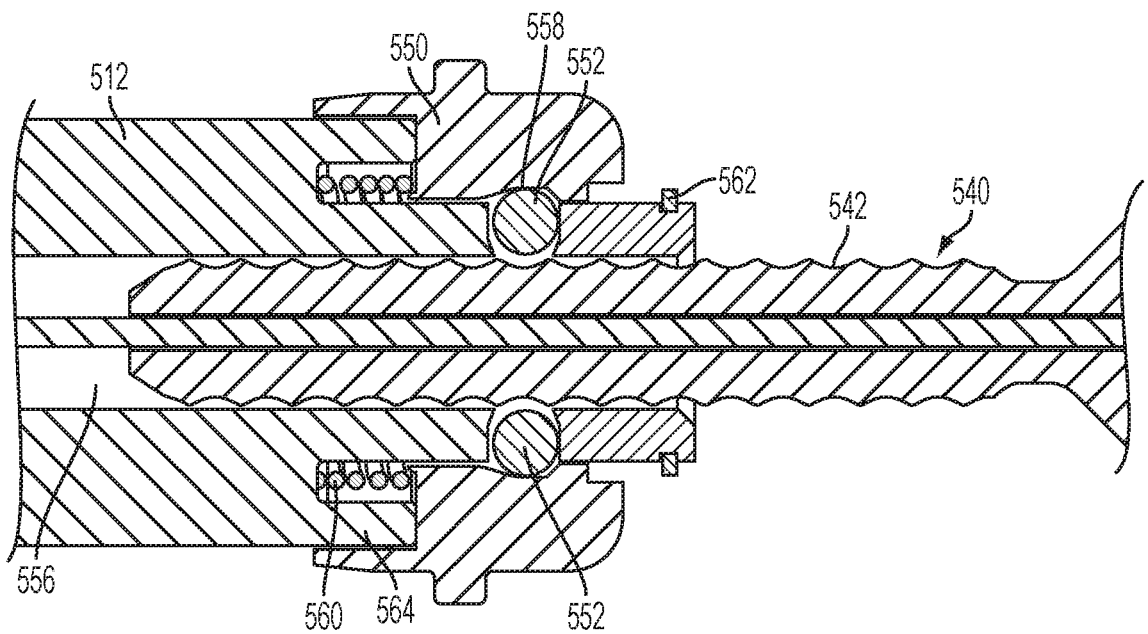
FIG. 5D is a longitudinal sectional view of the instrument of FIG. 5A shown with the release mechanism in a second position.

In some embodiments, as shown in FIGS. 4G-4H, the pitch of the threaded proximal portion 442 of the stylus 440 can be the same as the pitch of a threaded portion of the bone anchor assembly 400 or the bone tap. Accordingly, rotation of the elongate body 412 relative to the stylus 440 can be effective to withdraw the guide projection 402 from the bone anchor assembly 400 or the bone tap at the same rate as the bone anchor assembly or the bone tap is advanced into the bone. In other embodiments, the pitch of the threaded portion 442 can differ from that of the threaded portion of the bone anchor assembly 400 or the bone tap.

The handle portion 428 can be separable from the elongate body 412, and in some embodiments can be provided with the stylus 440 as a kit for use with various existing elongate bodies (e.g., modular drivers configured to mate with different types of bone anchors or bone taps).

Instruments with Release Mechanisms

FIGS. 5A-5D illustrate an exemplary embodiment of a surgical instrument 510 for driving a bone anchor 506 or a bone tap into bone. The instrument 510 can include an elongate body 512, a stylus 540, and a release mechanism 544 for selectively unlocking the stylus from the elongate body, for example to quickly withdraw the stylus or to index the stylus to an initial starting position.

A handle portion 528 can be formed at the proximal end of the elongate body 512 to allow the instrument 510 to be grasped by a surgeon. An engagement portion 514 can be formed at the distal end of the elongate body 512 and can be configured to engage a bone anchor assembly 500 (e.g., bone anchor assemblies of the type described above with respect to FIGS. 1A-1B). The engagement portion 514 can include a threaded surface 516 configured to engage corresponding threads formed in the receiver member 520 of the bone anchor assembly 500. The engagement portion 514 can also include a tip 518 disposed distally of the threaded surface 516 configured to engage a drive socket or a proximal surface of the bone anchor 506 or a compression cap (not shown) disposed within the receiver member 520. The tip 518 can have a diameter that is less than the diameter of the threaded portion 516. The engagement portion 514 can also be configured to engage a bone tap, or a bone tap can be formed integrally with the elongate body 512, in which case the engagement portion 514 can be omitted. One or more bulges or areas of increased diameter 546 can be formed along the length of the elongate body 512 to engage and stabilize extension sleeves 548 which may be coupled to the bone anchor assembly 500.

The elongate body 512 can be hollow or can include a central axial lumen extending longitudinally therethrough in which the stylus 540 can be positioned. The stylus 540 can include a proximal handle portion 538 and a threaded portion 542 disposed adjacent to the proximal handle portion. The stylus 540 can also include a guide projection 502 formed at the distal end thereof. The guide projection 502 can be formed integrally with the stylus 540 or can be selectively coupled thereto, for example using a snap-fit or threaded coupling. The guide projection 502 can be configured for insertion through a cannulation formed in the bone anchor assembly 500 or in a bone tap. The guide projection 502 can have a diameter that is less than the diameter of the threaded portion 516 and/or less than the diameter of the tip 518.

The threaded portion 542 of the stylus 540 can be configured to engage the release mechanism 544. In the illustrated embodiment, the release mechanism 544 includes a collar 550 that is slidably disposed around the elongate body 512 at a proximal end of the handle portion 528. The collar 550 can retain first and second lock balls 552 within respective openings formed in the sidewall of the elongate body. The lock balls 552 can be sized such that at least a portion of each lock ball fits within the space between adjacent threads on the threaded portion 542 of the stylus 540. The collar 550 can be slidable between a first position, shown in FIG. 5C, in which the stylus 540 can translate axially relative to the elongate body 512 only when the stylus is rotated relative to the elongate body and a second position, shown in FIG. 5D, in which the stylus is free to translate axially relative to the elongate body without being rotated relative to the elongate body.

In the first or "locked" position, a first portion 554 of the interior surface of the collar 550 can be positioned adjacent to the openings formed in the elongate body 512. The first portion 554 can have an inside diameter that is substantially the same as the outside diameter of the portion of the elongate body 512 around which the collar 550 is disposed. The first portion 554 can thus be effective to hold the lock balls 552 in a position in which they at least partially extend into the central lumen 556 of the elongate body 512 and engage the threaded portion 542 of the stylus 540. In the first position, portions of the lock balls 552 can fit within the space between adjacent threads on the stylus 540. The resulting interference can prevent the stylus 540 from translating axially relative to the elongate body 512 unless the stylus is rotated relative to the elongate body to advance each thread past the lock balls 552.

In the second or "unlocked" position, a second portion 558 of the interior surface of the collar 550 can be positioned adjacent to the openings formed in the elongate body 512. The second portion 558 can have a concave interior surface that defines a relief in which at least a portion of the lock balls 552 can be received. The second portion 558 can thus be configured to allow the lock balls 552 to move radially outward from the central lumen 556 of the elongate body 512 within their respective openings to disengage the stylus 540. In the second position, an axial force applied to the stylus 540 can cause the threads formed thereon to push the lock balls 552 radially outward, thereby releasing the stylus such that the force is effective to translate the stylus axially relative to the elongate body 512.

The release mechanism 544 can be biased towards either the first or second positions by a bias spring 560. In the illustrated embodiment, the release mechanism 544 is biased proximally towards the first, locked position. The bias spring 560 can be seated between a channel formed in the proximal end of the elongate body and a distal-facing surface of the collar 550.

While two lock balls 552 are shown in the illustrated embodiment in diametrically opposed positions, it will be appreciated that any number of lock balls can be used and that the lock balls can be placed in a variety of positions about the circumference of the collar 550. For example, a single lock ball 552 can be employed in some embodiments, or the release mechanism 544 can include four lock balls spaced equally 90 degrees apart about the circumference of the collar 550.

A retaining ring 562 can be positioned within a groove formed in the proximal end of the elongate body 512 such that the ring extends radially outward to form an end stop that limits proximal travel of the collar 550 relative to the elongate body. The elongate body 512 can also include a shoulder portion 564 configured to limit distal travel of the collar 550.

In some embodiments, the collar can have an interior surface that varies along the circumference of the collar, such that the collar can be rotated relative to the elongate body 512 (with or without axial translation) between a first or "locked" position and a second or "unlocked" position. For example, rotating the collar 90 degrees relative to the elongate body 512 can be effective to move the collar from the first position to the second position and vice versa. In the first position, first portions of the interior surface of the collar configured to hold the lock balls 552 in a position in which they at least partially extend into the central lumen 556 to engage the stylus 540 are disposed adjacent to the openings formed in the elongate body. In the second position, second portions of the interior surface of the collar configured to allow the lock balls 552 to move radially outward from the central lumen 556 to disengage the stylus 540 are disposed adjacent to the openings formed in the elongate body. The first and second portions of the interior surface can be disposed at the same position along the length of the collar, but can be disposed at different positions about the circumference of the collar. Accordingly, rotation of the collar relative to the elongate body 512 can be effective to move the collar from the first position to the second position, even if the collar is not translated longitudinally relative to the elongate body. While collar and lock ball configurations are shown and described herein, it will be appreciated that any of a variety of release mechanisms can be used instead or in addition.

The stylus 540 can be axially translatable between at least a first position in which the distal end of the guide projection 502 protrudes from the distal end of the bone anchor assembly 500 and a second position in which the distal end of the guide projection does not protrude from the distal end of the bone anchor assembly. The axial position of the guide projection 502 relative to the distal tip of the bone anchor 506 can be adjusted by translating the stylus 540 proximally or distally relative to the elongate body 512. In some embodiments, this axial translation can be accomplished by rotating the stylus 540 relative to the elongate body 512 in a first direction to advance the stylus along the release mechanism 544 and by rotating the stylus in a second, opposite direction to retract the stylus along the release mechanism. The axial translation can also be accomplished by positioning the release mechanism 544 in the "unlocked" configuration and applying a distally-directed or proximally-directed axial force to the stylus 540.

In some embodiments, the threaded portion 542 of the stylus 540 can be replaced with a series of grooves that do not form a continuous thread. In such embodiments, rotation of the stylus 540 relative to the elongate body 512 is not effective to translate the stylus axially relative to the elongate body. Rather, when the release mechanism 544 is in the first or "locked" position, the stylus 540 is maintained at a fixed axial position relative to the elongate body 512, regardless of whether the stylus is rotated relative to the elongate body.

The elongate body 512 can include a stop (not shown) configured to limit the degree to which the stylus 540 can be advanced in the distal direction to prevent over-insertion of the stylus. While a variety of stops can be used, in some embodiments, the stop is defined by a shoulder or section of the central lumen 556 having a diameter less than the diameter of the threaded portion 542. The stop can be adjustable based on the length of the bone anchor assembly 500 to be installed, such that the guide projection 502 cannot advance more than a predetermined distance beyond the distal tip of the bone anchor assembly (e.g., about 20 mm to about 25 mm beyond the distal tip).

The pitch of the threaded proximal portion 542 of the stylus 540 can be the same as the pitch of a threaded portion of the bone anchor assembly 500 or the bone tap. Accordingly, rotation of the elongate body 512 relative to the stylus 540 can be effective to withdraw the guide projection 502 from the bone anchor assembly 500 or the bone tap at the same rate as the bone anchor assembly or the bone tap is advanced into the bone. In other embodiments, the pitch of the threaded portion 542 can differ from that of the threaded portion of the bone anchor assembly 500 or the bone tap.

The handle portion 528 and the release mechanism 544 can be separable from the elongate body 512, and in some embodiments can be provided with the stylus 540 as a kit for use with various existing modular drivers (e.g., drivers configured to mate with different types of bone anchors or bone taps).

Instruments with Clutch Mechanisms

FIGS. 6A-6E illustrate an exemplary embodiment of a surgical instrument 610 for driving a bone anchor 606 or bone tap into bone. The instrument 610 can include an elongate body 612, a stylus 640, and a clutch mechanism 644 for allowing the stylus to slip distally relative to the elongate body while preventing the stylus from slipping proximally relative to the elongate body. In other words, the clutch mechanism 644 can allow the stylus 640 to translate axially in a distal direction relative to the elongate body 612 without requiring rotation relative to the elongate body, but can prevent the stylus from translating axially in a proximal direction relative to the elongate body unless the stylus is rotated relative to the elongate body.

A handle portion 628 can be formed at the proximal end of the elongate body 612 to allow the instrument 610 to be grasped by a surgeon. An engagement portion 614 can be formed at the distal end of the elongate body 612 and can be configured to engage a bone anchor assembly 600 (e.g., bone anchor assemblies of the type described above with respect to FIGS. 1A-1B). The engagement portion 614 can include a threaded surface 616 configured to engage corresponding threads formed in the receiver member 620 of the bone anchor assembly 600. The engagement portion 614 can also include a tip 618 disposed distally of the threaded surface 616 configured to engage a drive socket or a proximal surface of the bone anchor 606 or a compression cap (not shown) disposed within the receiver member 620. The tip 618 can have a diameter that is less than the diameter of the threaded portion 616. The engagement portion 614 can also be configured to engage a bone tap, or a bone tap can be formed integrally with the elongate body 612, in which case the engagement portion can be omitted. One or more bulges or areas of increased diameter 646 can be formed along the length of the elongate body 612 to engage and stabilize extension sleeves 648 which may be coupled to the bone anchor assembly 600.

The elongate body 612 can be hollow or can include a central axial lumen extending longitudinally therethrough in which the stylus 640 can be positioned. The stylus 640 can include a proximal handle portion 638 and a threaded portion 642 disposed adjacent to the proximal handle portion. The threaded portion 642 can include a unidirectional thread form. The stylus 640 can also include a guide projection 602 formed at the distal end thereof. The guide projection 602 can be formed integrally with the stylus 640 or can be selectively coupled thereto, for example using a snap-fit or threaded coupling. The guide projection 602 can be configured for insertion through a cannulation formed in the bone anchor assembly 600 or in a bone tap. The guide projection 602 can have a diameter that is less than the diameter of the threaded portion 616 and/or less than the diameter of the tip 618.

Figure 6A:
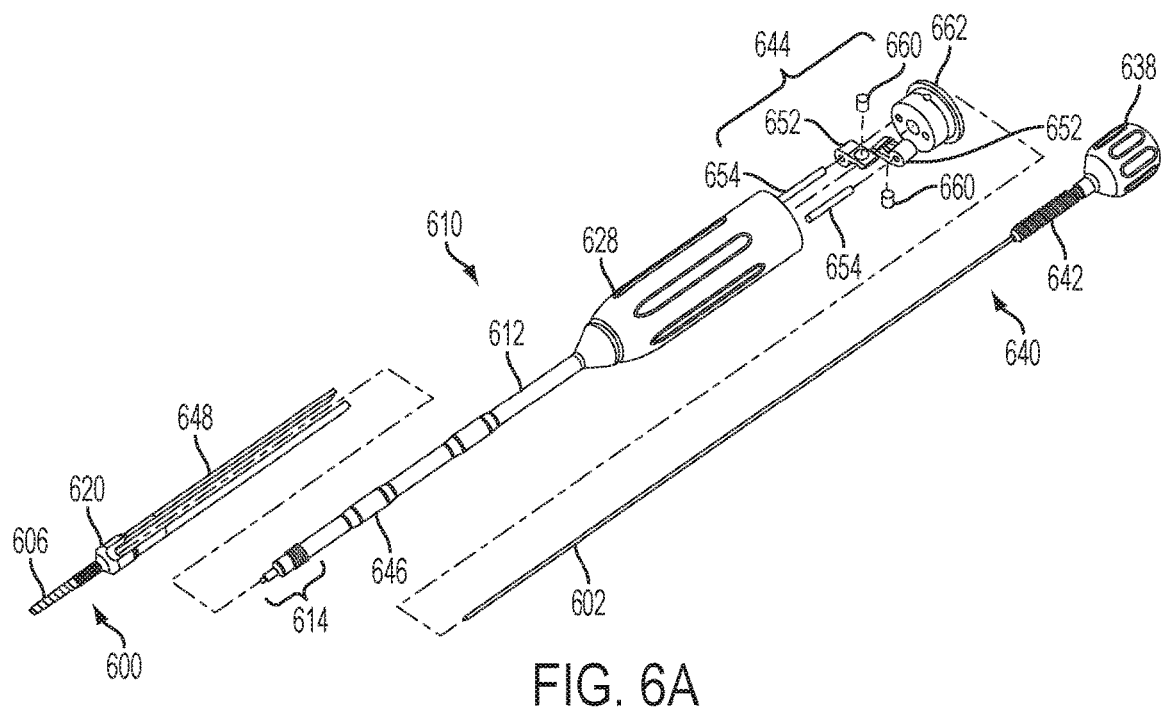
FIG. 6A is an exploded view of a bone anchor assembly and an instrument for driving the bone anchor assembly that includes a clutch mechanism.
Figure 6B:
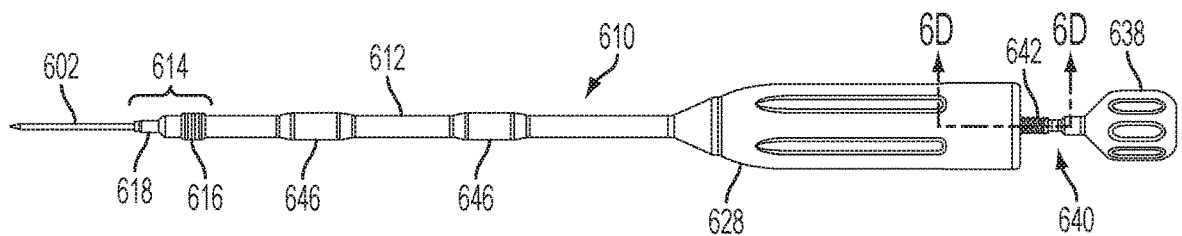
FIG. 6B is a side view of the instrument of FIG. 6A.
Figure 6C:
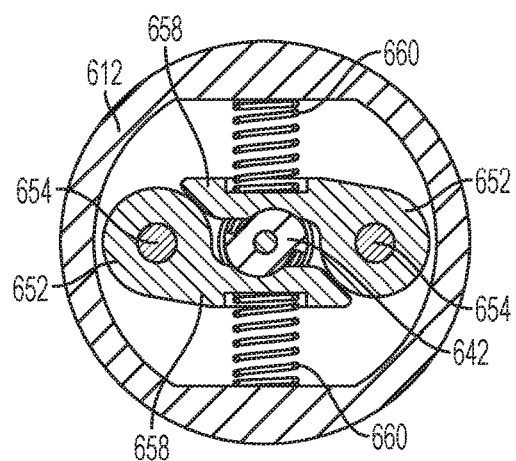
FIG. 6C is a transverse sectional view of the instrument of FIG. 6A.
Figure 6D:
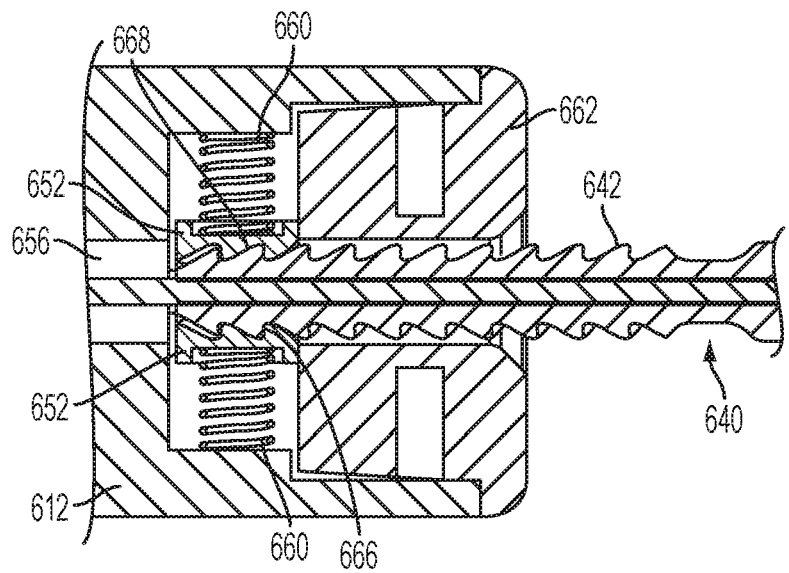
FIG. 6D is a longitudinal sectional view of the instrument of FIG. 6A shown with the clutch mechanism in a first position.
Figure 6E:
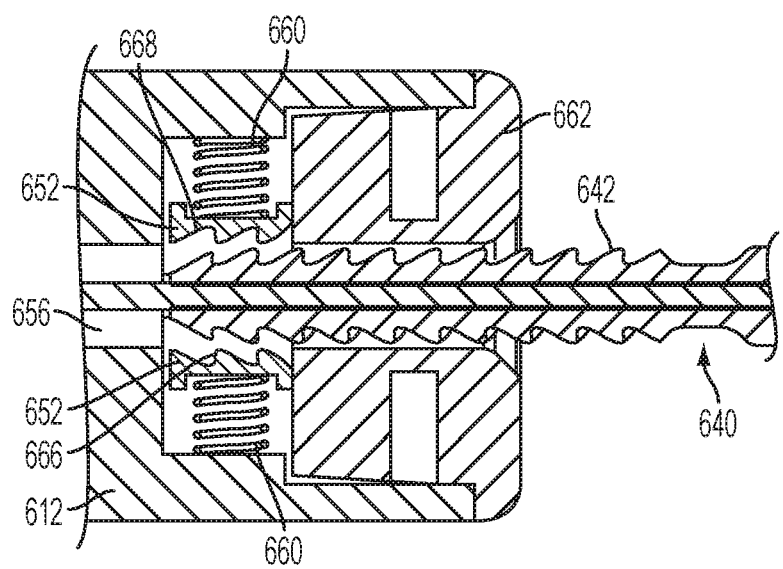
FIG. 6E is a longitudinal sectional view of the instrument of FIG. 6A shown with the clutch mechanism in a second position.

The threaded portion 642 of the stylus 640 can be configured to engage the clutch mechanism 644. In the illustrated embodiment, the clutch mechanism 644 includes first and second clutch plates 652 which are movable (e.g., pivotable) into and out of engagement with the threaded portion 642 of the stylus 640. As shown in FIG. 6C, the clutch plates 652 can be mounted on pivot pins 654 such that they can rotate about respective axes that are parallel to the central longitudinal axis of the elongate body 612. The clutch plates 652 can include wings 658 having stylus-engaging portions that conform to the exterior contour of the threaded portion 642 of the stylus 640. In particular, the stylus-engaging surfaces can include teeth formed thereon that are substantial negatives of the threads formed on the stylus 640. Respective bias springs 660 can bias the clutch plates 652 into engagement with the stylus 640. The clutch plates 652 can be movable between a first or "engaged" position, shown in FIG. 6D and a second or "disengaged" position, shown in FIG. 6E.

In the first or "engaged" position, the clutch plates 652 can be pressed into engagement with the stylus 640 by the bias springs 660 and surfaces 666 of the teeth that extend substantially perpendicular to the longitudinal axis of the elongate body 612 can catch against the threads 642 of the stylus to prevent the stylus from slipping proximally relative to the clutch plates.

In the second or "disengaged" position, an axially-directed force applied to the stylus 640 in the distal direction can cause ramped surfaces 668 of the teeth to cam over the threads 642 of the stylus. This can cause the clutch plates 652 to pivot about the pivot pins 654, momentarily disengaging the stylus 640 and allowing the stylus to slip distally relative to the clutch plates. Once the stylus 640 advances distally past one or more previously-engaged threads, the bias springs 660 can cause the clutch plates 652 to rotate back into the first, engaged position.

The teeth can thus act as a ratchet and the threads as a pawl to facilitate stepwise advancement of the stylus 640 within the elongate body 612 while preventing the stylus from being backed out proximally relative to the elongate body. Depending on the magnitude of the force applied to the stylus 640, one or more threads can be traversed with each impact. The clutch mechanism 644 can be configured to emit audible or tactile feedback as each thread is traversed, allowing the surgeon to infer the degree to which the stylus 640 has been advanced relative to the elongate body 612. The threads 642 on the stylus 640 and the teeth on the clutch plates 652 can be sized according to a predetermined geometry, such that slipping the stylus by one thread equates to a known advancement distance (e.g., 3 mm per click). The elongate body 612 can include a stop (not shown) configured to limit the degree to which the stylus 640 can be advanced in the distal direction to prevent over-insertion of the stylus. While a variety of stops can be used, in some embodiments, the stop is defined by a shoulder or section of the central lumen 656 having a diameter less than the diameter of the threaded portion 642. The stop can be adjustable based on the length of the bone anchor assembly 600 to be installed, such that the guide projection 602 cannot advance more than a predetermined distance beyond the distal tip of the bone anchor assembly 600 (e.g., about 20 mm to about 25 mm beyond the distal tip).

While two clutch plates 652 are shown in the illustrated embodiment in diametrically opposed positions, it will be appreciated that any number of clutch plates can be used and that the clutch plates can be placed in a variety of positions about the circumference of the stylus 640. For example, a single clutch plate 652 can be employed in some embodiments, or the clutch mechanism 644 can include four clutch plates spaced equally 90 degrees apart about the circumference of the stylus 640.

The clutch mechanism 644 can be disposed within a bore formed in the proximal end of the handle portion 628 of the elongate body 612. A plug 662 can be positioned within the bore to retain the clutch mechanism 644 therein. While a ratchet and pawl type clutch is shown in the illustrated embodiment, it will be appreciated that any of a variety of clutch mechanisms can be used instead or in addition.

The stylus 640 can be axially translatable between at least a first position in which the distal end of the guide projection 602 protrudes from the distal end of the bone anchor assembly 600 and a second position in which the distal end of the guide projection does not protrude from the distal end of the bone anchor assembly. The axial position of the guide projection 602 relative to the distal tip of the bone anchor 606 can be adjusted by translating the stylus 640 proximally or distally relative to the elongate body 612. In some embodiments, this axial translation can be accomplished by rotating the stylus 640 relative to the elongate body 612 in a first direction to advance the stylus along a threaded surface of the clutch plates 652 and by rotating the stylus in a second, opposite direction to retract the stylus along the threaded surface of the clutch plates. The axial translation can also be accomplished by applying a distally-directed force to the stylus 640 to cause the stylus to slip along the clutch plates 652.

Alternatively, the threads formed on the stylus 640 and/or on the clutch plates 652 can be discontinuous such that rotation of the stylus relative to the elongate body 612 does not change the axial position of the stylus relative to the elongate body. In such embodiments, axial translation can be accomplished only by applying a distally-directed force to the stylus 640 to cause the stylus to slip along the clutch plates 652.

In some embodiments, a clutch lockout (not shown) can be provided to maintain the clutch 644 in the disengaged position, which can allow the stylus 640 to be retracted proximally. For example, a sleeve can be slidably disposed within the central lumen 656 coaxially around the threaded portion 642 of the stylus 640. The sleeve can be advanced distally to push the clutch plates 652 out of engagement with the stylus 640, thereby locking the clutch 644 in the disengaged position. The sleeve can also be retracted proximally to release the clutch plates 652 back into engagement with the stylus 640. A locking mechanism can also be provided to maintain the clutch 644 in the engaged position, which can prevent the stylus 640 from advancing distally relative to the elongate body 612 when an axial force is applied thereto. For example, one or more set screws, lock pins, collars, or sleeves can be disposed in the elongate body 612 to selectively hold the clutch plates 652 in engagement with the stylus 640.

The pitch of the threaded proximal portion 642 of the stylus 640 can be the same as the pitch of a threaded portion of the bone anchor assembly 600 or the bone tap. Accordingly, rotation of the elongate body 612 relative to the stylus 640 can be effective to withdraw the guide projection 602 from the bone anchor assembly 600 or the bone tap at the same rate as the bone anchor assembly or the bone tap is advanced into the bone. In other embodiments, the pitch of the threaded portion 642 can differ from that of the threaded portion of the bone anchor assembly 600 or the bone tap.

The handle portion 628 and the clutch mechanism 644 can be separable from the elongate body 612, and in some embodiments can be provided with the stylus 640 as a kit for use with various existing modular drivers (e.g., drivers configured to mate with different types of bone anchors or bone taps).

Adjustable-Length Stylus

Figure 7A:
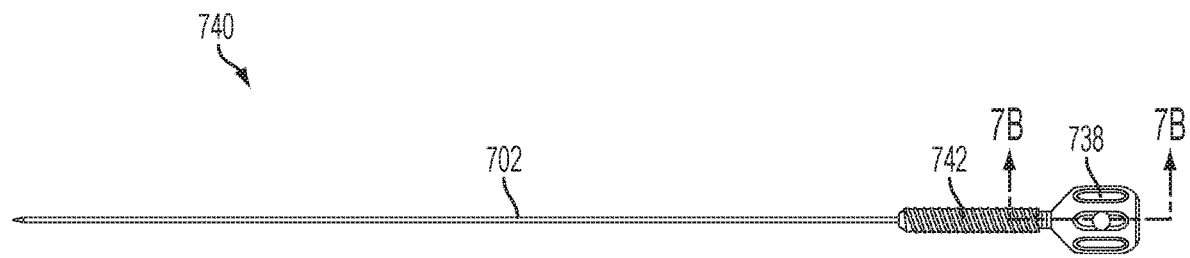
FIG. 7A is a side view of an adjustable-length stylus.
Figure 7B:
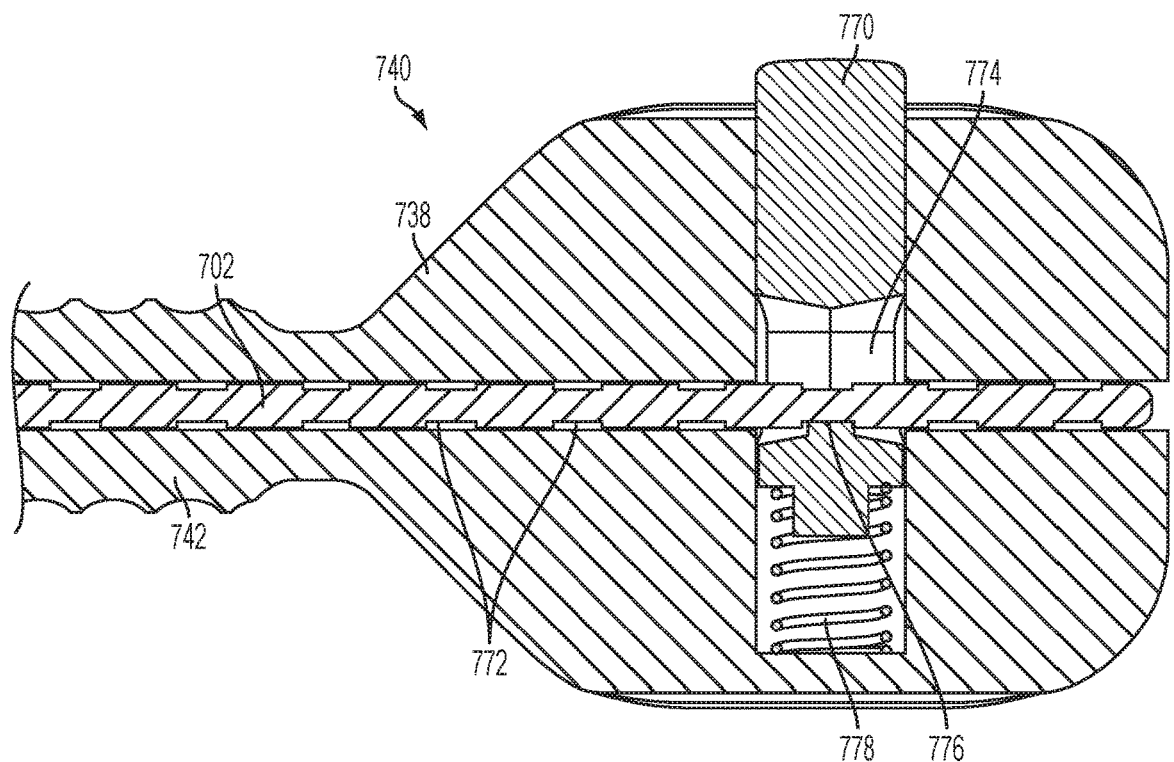
FIG. 7B is a longitudinal sectional view of the stylus of FIG. 7A.

FIGS. 7A-7B illustrate an exemplary embodiment of an adjustable-length stylus 740 that can be used with any of the instruments 410, 510, 610 described above. The stylus 740 is similar in structure and operation to those described above, except as described below. As shown, the guide projection 702 can be a separate component from the handle portion 738. The guide projection 702 can be slidably disposed within a central lumen of the handle portion 738 such that the guide projection 702 is axially translatable relative to the handle portion 738. Axial translation of the guide projection 702 relative to the handle portion 738 can thus be effective to adjust the working length of the stylus 740 (e.g., the distance between the distal tip of the guide projection 702 and the threaded proximal portion 742). The handle portion 738 can include a release button 770 configured to selectively engage one or more grooves 772 formed in the guide projection 702. In particular, the release button 770 can include a central lumen 774 through which the guide projection 702 extends. A projection 776 sized to engage one or more of the grooves 772 can extend radially inward from the sidewall of the lumen 774. The release button 770 can be slidable relative to the handle portion 738, e.g., in a direction transverse to the longitudinal axis of the guide projection 702, such that the release button is movable between a first position in which the projection 776 engages one or more of the grooves 772 to fix the axial position of the guide projection 702 relative to the handle portion 738, and a second position in which the projection 776 does not engage any of the grooves 772 and the axial position of the guide projection 702 relative to the handle portion 738 can be adjusted freely. A bias spring 778 can be disposed between the handle portion 738 and the release button 770 and can be configured to bias the release button 770 towards the first position, as shown in FIG. 7B.

The ability to adjust the working length of the stylus 740 can advantageously allow the stylus 740 to be used with a plurality of bone anchor assemblies, each of the bone anchor assemblies having a different length.

Methods

Figure 8A:
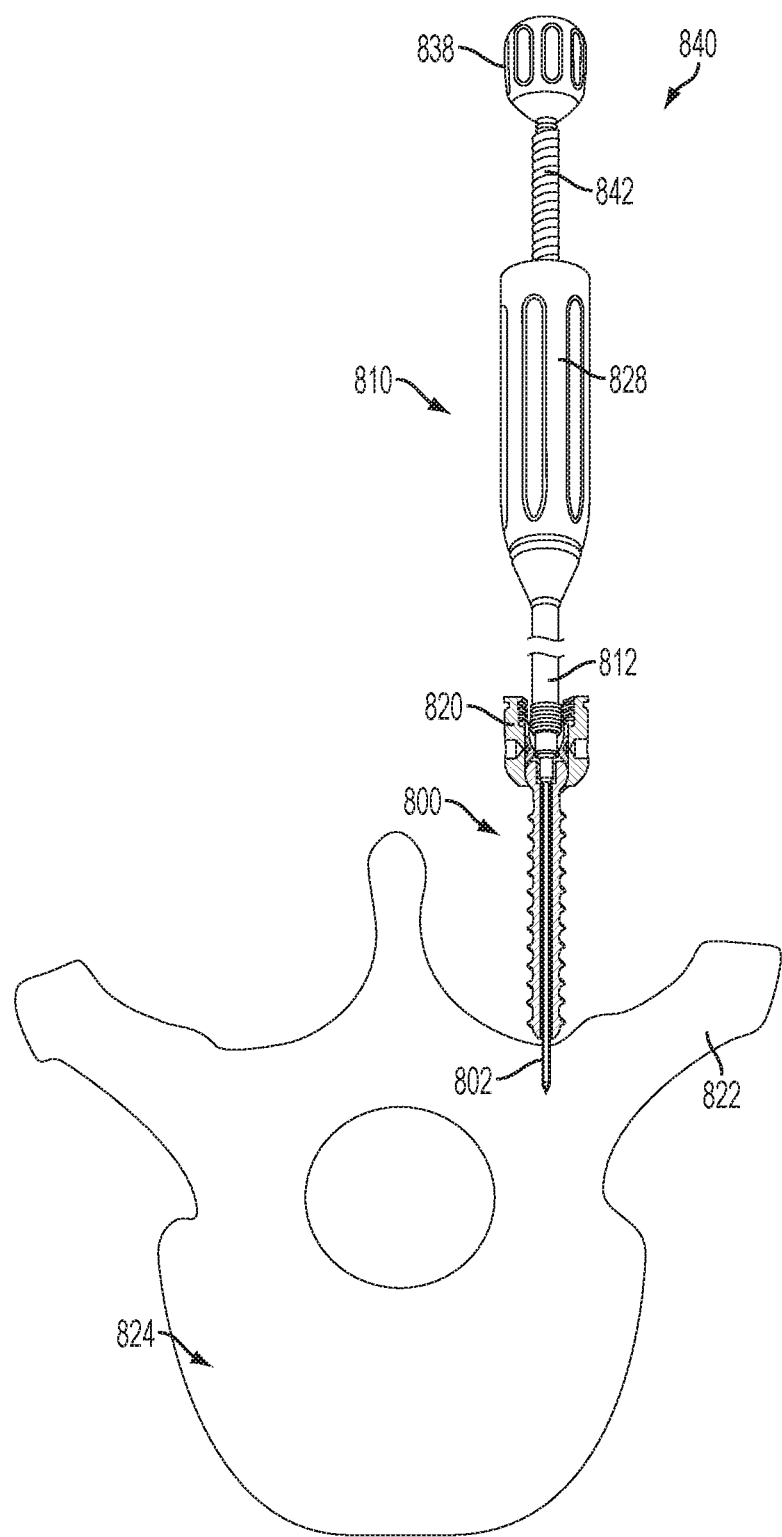
FIG. 8A is a schematic view of a bone anchor assembly and an instrument for driving the bone anchor assembly shown with a guide projection of the instrument docked in a pedicle.
Figure 8B:
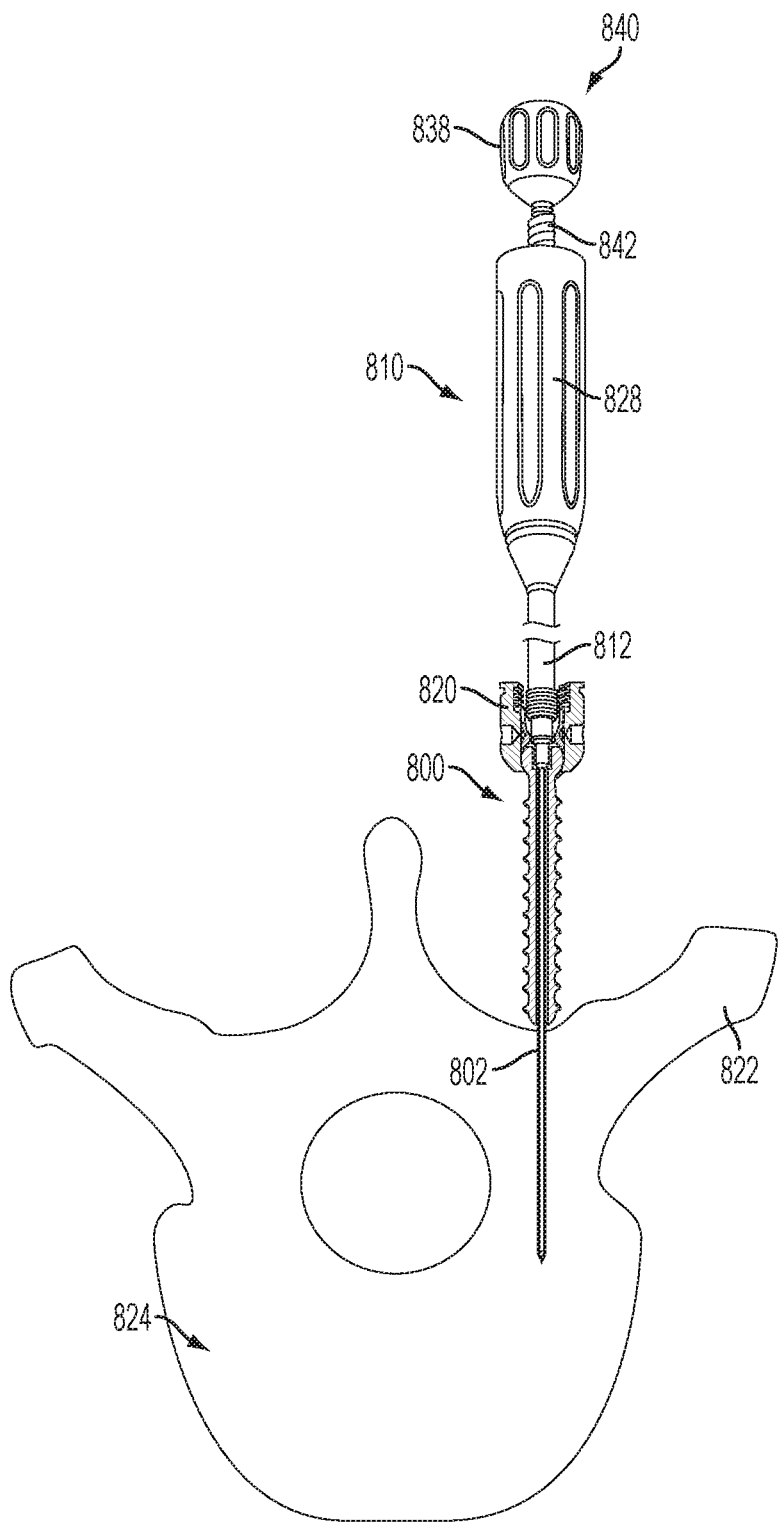
FIG. 8B is a schematic view of the bone anchor assembly and instrument of FIG. 8A shown after the guide projection is advanced into the pedicle.
Figure 8C:
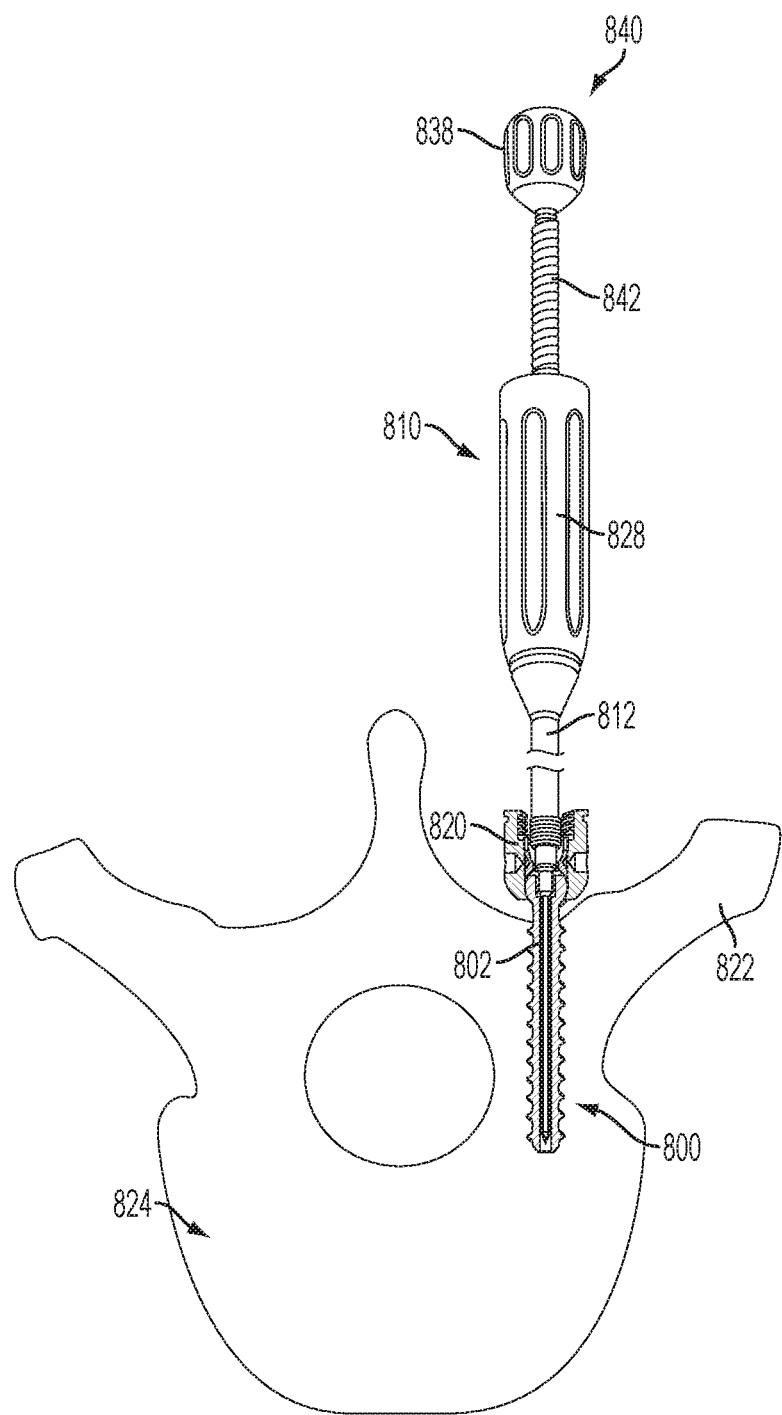
FIG. 8C is a schematic view of the instrument and bone anchor assembly of FIG. 8A shown after the bone anchor assembly is advanced into the pedicle.

FIGS. 8A-8C schematically illustrate a method of using an instrument 810 having a stylus 840 with an integrated guide projection 802 to drive a bone anchor assembly 800 into bone 824. The method detailed below can be used with any of the instruments disclosed above (e.g., the instruments 410, 510, 610), with any necessary modifications being apparent to one skilled in the art having read the above disclosure.

To begin with, an incision can be made to access the bone to which the bone anchor assembly 800 is to be coupled (e.g., a pedicle 822 of one of the patient's vertebrae 824). The bone anchor assembly 800 can be coupled to the instrument 810 and advanced through the incision to position the bone anchor assembly in proximity to the bone surface. The stylus 840 can be indexed to an initial position based on various parameters such as the length of the bone anchor assembly 800. This can be accomplished, for example, by actuating a release mechanism and/or clutch mechanism of the instrument 810, by rotating the stylus 840 relative to the elongate body 812 to index the position of the stylus, or by adjusting the length of the stylus (when an adjustable-length stylus such as the stylus 740 described above is used). In some embodiments, the stylus 840 can be initially positioned such that the guide projection 802 protrudes from the distal end of the bone anchor assembly 800. It will be appreciated, however, that the stylus 840 can be initially positioned such that the guide projection 802 does not protrude from the distal end of the bone anchor assembly 800.

As shown in FIG. 8A, the protruding guide projection 802 of the stylus 840 can be docked into the pedicle 822 by tapping or urging the instrument 810 distally towards the bone surface. As shown in FIG. 8B, the stylus 840 can be rotated relative to the elongate body 812 to mechanically advance the guide projection 802. Alternatively, or in addition, an impact force can be applied to the stylus 840 in the distal direction while a release or clutch mechanism is actuated, to advance the guide projection 802 into the bone 824. The proper trajectory and depth can be confirmed with fluoroscopy. The insertion depth can also be inferred by the surgeon (e.g., based on the number of rotations of the stylus 840, audible or tactile feedback generated by a clutch mechanism, or based on the stylus hitting a stop disposed in or on the elongate body 812).

Once the guide projection 802 is advanced to the desired depth, the handle portion 828 of the elongate body 812 can be rotated relative to the bone 824 to drive the bone anchor assembly 800 into the opening formed by the guide projection 802, as shown in FIG. 8C. At the same time, the handle portion 838 of the stylus 840 can be maintained in a fixed rotational position relative to the bone 824 (i.e., such that the handle portion 828 of the elongate body 812 rotates relative to the handle portion 838 of the stylus 840 as the anchor assembly 800 is driven into the bone 828). As a result, the guide projection 802 can be maintained at a constant depth within the bone 828 as the bone anchor assembly 800 is advanced distally over the guide projection, or can be withdrawn proximally as the bone anchor assembly is advanced distally. In embodiments in which the threaded portion 842 of the stylus 840 has the same pitch as the threaded portion of the bone anchor assembly 800, retraction of the guide projection 802 into the bone anchor assembly can occur at the same rate as the advancement of the bone anchor assembly, such that the guide projection remains at a substantially fixed depth within the bone 824.

When the bone anchor assembly 800 is driven to the desired depth, the stylus 840 and the elongate body 812 can be detached from the bone anchor assembly 800 and removed from the incision. Subsequent steps, such as affixing a spinal rod or other component to the receiver member 820 can then be performed.

As noted above, the bone anchor assembly 800 can include various self-tapping features to facilitate insertion into the bone 824 and to prevent the bone from fracturing during anchor insertion. In some instances, patient anatomy or surgeon preferences can require the bone 824 to be tapped before inserting the bone anchor assembly 800. In such instances, the above method can be modified to use embodiments of the instrument 810 that include an integral bone tap or which are coupled to a bone tap via the engagement portion. After the bone opening is tapped, the handle portion 838 of the stylus 840 can be removed and the bone tap and driver (if applicable) can be withdrawn proximally out of the incision, leaving the stylus 840 in place. The driver can then be coupled to a bone anchor assembly 800, or replaced with a separate instrument coupled to a bone anchor assembly, and then advanced over the stylus to position and drive the bone anchor assembly into the opening formed by the tap.

It should be noted that any ordering of method steps implied by the drawings or description herein is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present invention.

The guide projections of the various embodiments disclosed herein can be rigid or flexible. The guide projections can be formed from a radiopaque material to facilitate visualization under fluoroscopy and other imaging techniques. Other components of the devices disclosed herein (e.g., elongate body portions, handle portions, and the like) can be formed from a radiolucent material so as not to interfere with visualization of the guide projection. Exemplary radiolucent materials include carbon fiber and high-strength polymers. The devices disclosed herein can also be compatible with image-guide surgical systems and with stimulation systems (e.g., neuromonitoring systems typically used to monitor for pedicle breach and to confirm screw or instrument placement).

The methods and devices disclosed herein can provide a number of advantages. For example, in some embodiments, the time required to target and place the bone anchor assembly can be reduced, the radiation exposure to the patient and to the surgical staff can be reduced, and procedural steps such as needle placement, guidewire insertion and removal, and tapping can be eliminated. By way of further example, in some embodiments, inadvertent advancement of instrumentation can be eliminated by controlling the guide projection depth throughout the procedure, risk of removing a guidewire during removal of a needle or tap can be eliminated, and bending or kinking of a guidewire can be prevented.

The devices and methods disclosed herein can be used in minimally-invasive surgery and/or open surgery. While the devices and methods disclosed herein are generally described in the context of advancing a bone anchor into a pedicle, it will be appreciated that the methods and devices disclosed herein can be used with any human or animal bone, implant, non-living object, and so forth.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

The invention claimed is:

1. A driver instrument, comprising:
   an elongate body that extends from a proximal end to a distal end and defines a central axial lumen therebetween;
   a receiving portion formed at the proximal end of the elongate body;
   an engagement portion formed at the distal end of the elongate body that is configured to engage a bone anchor assembly;
   a stylus comprising a guide projection that is configured to be received through the central axial lumen and be axially translatable proximally or distally relative to the elongate body such that, when the engagement portion is engaged with a bone anchor assembly, the stylus is axially translatable between at least a first position in which a distal end of the guide projection protrudes from a distal tip of the bone anchor assembly and a second position in which the distal end of the guide projection does not protrude from the distal tip of the bone anchor assembly;
   a threaded portion disposed proximal to the stylus and configured to engage a corresponding threaded portion of the central axial lumen of the elongate body to secure the stylus to the elongate body; and
   a proximal handle portion disposed adjacent to the threaded portion and configured to move relative to the elongate body to axially translate the stylus, the proximal handle portion receiving a portion of the receiving portion therethrough.

2. The driver of claim 1, wherein the proximal handle portion comprises a collar having an opening formed therein configured to receive the elongate body therethrough.

3. The driver of claim 1, wherein the guide projection is formed integrally with the stylus or is selectively coupled thereto using a snap-fit or threaded coupling.

4. The driver of claim 1, wherein the guide projection extends beyond the distal tip of the bone anchor assembly by a distance between about 0.1 mm and about 100 mm.

5. The driver of claim 4, wherein the guide projection extends for approximately a range of about 20 mm to about 25 mm beyond the distal tip of the bone anchor assembly.

6. The driver of claim 1, wherein an amount that the guide projection protrudes from the distal end of the bone anchor assembly is based on one or more of length of the bone anchor, an anatomy of a patient, a location at which the bone anchor assembly is to be positioned, or a type of procedure in which the bone anchor assembly is involved.

7. The driver of claim 1, further comprising a stop configured to limit a degree to which the stylus is advanced in the distal direction to prevent over-insertion of the stylus.

8. The driver of claim 7, wherein the stop comprises a shoulder that prevents the guide projection from advancing beyond a predetermined distance beyond the distal tip of the bone anchor assembly.

9. The driver of claim 1, further comprising a handle located at the proximal end of the elongate body to facilitate grasping of the driver instrument.

10. The driver of claim 1, wherein the engagement portion further comprises a threaded surface configured to engage corresponding threads of the bone anchor assembly.

11. The driver of claim 10, wherein the engagement portion further comprises a tip disposed distally of the threaded surface configured to engage a drive socket or a proximal surface of the bone anchor.

12. The driver of claim 11, wherein the tip has a diameter that is smaller than a diameter of the threaded portion.

13. A surgical method, comprising:
   making an incision to a target site within a patient;
   advancing a bone anchor assembly through the incision, the bone anchor assembly being coupled to an inserter instrument having:
      an elongate body that extends from a proximal end to a distal end and defines a central axial lumen therebetween;
      an engagement portion formed at the distal end of the elongate body that is configured to engage a bone anchor assembly;
      a stylus having a guide projection that is configured to be received through the central axial lumen and extend through the bone anchor assembly to be axially translatable between at least a first position in which a distal end of the guide projection protrudes from a distal tip of the bone anchor assembly and a second position in which the distal end of the guide projection does not protrude from the distal tip of the bone anchor assembly; and
      a collar disposed around the elongate body that moves relative to the elongate body to engage the elongate body and actuate the stylus to translate axially, the collar being disposed distal to a proximal-most end of the stylus;
   positioning the bone anchor assembly at the target site such that a distal end of the guide projection is positioned against a bone surface at the target site;
   distally tapping the inserter instrument to dock the guide projection in the bone surface; and
   rotating the inserter instrument to advance the bone anchor assembly into the bone.

14. The method of claim 13, further comprising adjusting a position of the stylus relative to the bone anchor assembly to the first position.

15. The method of claim 13, wherein the guide projection is docked to the bone surface under fluoroscopic guidance.

16. The method of claim 13, further comprising, before or after advancing the bone anchor assembly into the bone, sliding one or more bone anchor extensions coaxially over the elongate body for coupling to a receiver member of the bone anchor assembly.

17. The method of claim 13, further comprising manipulating the collar to allow advancement of the stylus through the elongate body while grasping the elongate body to provide a countertorque thereto.

18. The method of claim 13, wherein an amount that the distal end of the guide projection protrudes from the distal tip of the bone anchor assembly is based on one or more of a length of the bone anchor, an anatomy of a patient, a location at which the bone anchor assembly is to be positioned, or a type of procedure in which the bone anchor assembly is involved.

19. The method of claim 13, further comprising rotating the elongate body relative to the stylus to withdraw the guide projection from the bone anchor assembly at the same rate as the bone anchor assembly is advanced into the bone.

20. The method of claim 13, further comprising adjusting a stop based on a length of the bone anchor assembly to be installed, such that the guide projection cannot advance more than a predetermined distance beyond the distal tip of the bone anchor assembly.

21. A driver instrument, comprising:
- an elongate body that extends from a proximal end to a distal end and defines a central axial lumen therebetween;
- a receiving portion formed at the proximal end of the elongate body;
- an engagement portion formed at the distal end of the elongate body that is configured to engage a bone anchor assembly;
- a stylus comprising a guide projection that is configured to be received through the central axial lumen and be axially translatable proximally or distally relative to the elongate body such that, when the engagement portion is engaged with a bone anchor assembly, the stylus is axially translatable between at least a first position in which a distal end of the guide projection protrudes from a distal tip of the bone anchor assembly and a second position in which the distal end of the guide projection does not protrude from the distal tip of the bone anchor assembly; and
- a collar having an opening formed therein configured to receive the elongate body therethrough;
- wherein the collar is rotatable relative to the receiving portion to facilitate axial translation of the stylus between the first position and the second position while maintaining the elongate body position.

* * * * *